(12) United States Patent
Soza

(10) Patent No.: US 9,693,725 B2
(45) Date of Patent: Jul. 4, 2017

(54) METHODS, APPARATUSES AND SYSTEMS FOR DIAGNOSIS AND TREATMENT OF MOOD DISORDERS

(71) Applicant: Ana Maria Soza, Santiago (CL)

(72) Inventor: Ana Maria Soza, Santiago (CL)

( * ) Notice: Subject to any disclaimer, the term of this patent is extended or adjusted under 35 U.S.C. 154(b) by 96 days.

(21) Appl. No.: 13/780,352

(22) Filed: Feb. 28, 2013

(65) Prior Publication Data

US 2013/0225914 A1     Aug. 29, 2013

Related U.S. Application Data

(60) Provisional application No. 61/604,185, filed on Feb. 28, 2012.

(51) Int. Cl.
*A61B 5/16*        (2006.01)
*A61F 7/12*        (2006.01)
(Continued)

(52) U.S. Cl.
CPC ............ *A61B 5/165* (2013.01); *A61B 5/4836* (2013.01); *A61B 5/4863* (2013.01); *A61F 7/00* (2013.01);
(Continued)

(58) Field of Classification Search
CPC .......... A61M 21/00; A61M 2021/0005; A61M 2021/0044; A61M 2021/005;
(Continued)

(56) References Cited

U.S. PATENT DOCUMENTS 6,383,150 B1   5/2002   Stewart et al.
7,285,099 B1   10/2007   Peterka
(Continued)

FOREIGN PATENT DOCUMENTS

EP    1 112 104 A1    7/2001
EP    1 191 972 A1    4/2002
(Continued)

OTHER PUBLICATIONS

International Search Report and Written Opinion mailed Nov. 1, 2013 for Application No. PCT/IB2013/00871.
(Continued)

*Primary Examiner* — Charles A Marmor, II
*Assistant Examiner* — Thaddeus Cox
(74) *Attorney, Agent, or Firm* — Wolf, Greenfield & Sacks, P.C.

(57) ABSTRACT

A method and apparatus for diagnosing and/or treating mood disorders, such as depression, is provided. Right vestibular function in subjects diagnosed with a mood disorder is diminished compared with subjects who do not have a mood disorder. Accordingly, a method and apparatus for determining right vestibular function in a subject is provided, from which a diagnosis of a mood disorder may be determined. Stimulation of the vestibular system of a subject diagnosed with a mood disorder may reduce symptoms of the mood disorder in the subject. A method and apparatus for registering a subject's response to stimulation of the vestibular system and providing therapeutic vestibular stimulation based on the subject's response is provided. A subject's response to stimulation of the vestibular system may be based on measurements of nystagmus in the subject.

34 Claims, 9 Drawing Sheets

(51) Int. Cl.
| | |
|---|---|
| A61B 5/00 | (2006.01) |
| A61F 7/00 | (2006.01) |
| G06F 19/00 | (2011.01) |
| A61M 21/02 | (2006.01) |
| A61B 5/0496 | (2006.01) |
| A61N 5/06 | (2006.01) |
| A61M 21/00 | (2006.01) |

(52) U.S. Cl.
CPC ......... *A61M 21/02* (2013.01); *G06F 19/3481* (2013.01); *A61B 5/0496* (2013.01); *A61F 2007/0005* (2013.01); *A61F 2007/0059* (2013.01); *A61M 2021/0027* (2013.01); *A61M 2021/0044* (2013.01); *A61M 2021/0066* (2013.01); *A61M 2205/505* (2013.01); *A61N 5/0618* (2013.01)

(58) Field of Classification Search
CPC ......... A61M 2021/0022; A61B 5/0496; A61B 5/165; A61B 5/4836; A61B 5/4863; A61N 5/0618
USPC .......................................................... 600/28
See application file for complete search history.

(56) References Cited

U.S. PATENT DOCUMENTS

| | | | |
|---|---|---|---|
| 7,539,543 | B2 | 5/2009 | Schiff et al. |
| 7,933,654 | B2 | 4/2011 | Gong et al. |
| 8,041,429 | B2 | 10/2011 | Kirby |
| 8,262,717 | B2 | 9/2012 | Rogers et al. |
| 8,355,788 | B2 | 1/2013 | Mechlenburg et al. |
| 2000/0076580 | | 12/2000 | Kalik et al. |
| 2003/0195588 | A1 | 10/2003 | Fischell et al. |
| 2004/0138593 | A1 | 7/2004 | Maher |
| 2005/0101877 | A1 | 5/2005 | Miller et al. |
| 2005/0240253 | A1 | 10/2005 | Tyler et al. |
| 2006/0100671 | A1 | 5/2006 | Ridder et al. |
| 2006/0161218 | A1 | 7/2006 | Danilov |
| 2009/0240172 | A1* | 9/2009 | Fernandez Tournier et al. ........................ 600/595 |
| 2009/0312817 | A1 | 12/2009 | Hogle et al. |
| 2010/0030301 | A1 | 2/2010 | Milojevic et al. |
| 2010/0041961 | A9 | 2/2010 | Epley |
| 2010/0094161 | A1 | 4/2010 | Frank et al. |
| 2010/0198318 | A1 | 8/2010 | Rogers |
| 2010/0211142 | A1 | 8/2010 | Rogers et al. |
| 2011/0028872 | A1* | 2/2011 | Kevin .................... G09B 19/00 601/86 |
| 2011/0137104 | A1 | 6/2011 | Phillips et al. |
| 2011/0245633 | A1* | 10/2011 | Goldberg ............... A61B 5/681 600/301 |
| 2012/0289869 | A1 | 11/2012 | Tyler |
| 2012/0295778 | A1 | 11/2012 | Johansson et al. |
| 2012/0316625 | A1 | 12/2012 | Smith et al. |
| 2013/0090520 | A1 | 4/2013 | Redfield et al. |
| 2013/0317576 | A1* | 11/2013 | Rogers ................... A61F 7/007 607/99 |

FOREIGN PATENT DOCUMENTS

| | | |
|---|---|---|
| EP | 2 168 551 A1 | 5/2010 |
| EP | 2 301 507 A1 | 3/2011 |
| EP | 1 181 073 B1 | 7/2011 |
| EP | 2 435 130 A1 | 4/2012 |
| WO | WO 2006/024102 A1 | 3/2006 |
| WO | WO 2009/068994 A2 | 6/2009 |
| WO | WO 2010/101641 A3 | 12/2010 |
| WO | WO 2010/135783 A1 | 12/2010 |
| WO | WO 2012/083126 A1 | 6/2012 |
| WO | WO 2012/177589 A1 | 12/2012 |
| WO | WO 2013/128293 | 9/2013 |

OTHER PUBLICATIONS

[No Author Listed], GyroStim: Innovative Technology, Inspiring Applications. Retrieved Jul. 28, 2014. <http://www.gyrostim.com/applications.html>. 2 pages.

[No Author Listed], VNG Nydiag Rotary Chair Datasheet. Interacoustics. Dec. 23, 2013. Retrieved Oct. 17, 2013. <http://support.interacoustics.com/downloads/nydiag/sales/brochures/brochure_rotarychair_us.pdf>.

[No Author Listed], 510(K) Summary of Safety and Effectiveness Nydiag 200 Rotary Chair (FDA) Dec. 23, 2010. To Establish Priority of previous document, titled VNG Nydiag Rotary Chair.

Dobie et al., Cognitive-behavioral management of motion sickness. Aviat Space Environ Med. Oct. 1994;65(10 Pt 2):C1-2.

Dodson, Vestibular stimulation in mania: a case report. J Neurol Neurosurg Psychiatry. Jan. 2004;75(1):168-9.

Epigee, The history of women's mental illness. Nov. 2011. Retrieved on Oct. 8, 2013. <http://web.archive.org/web/20111101041755/http://jnnp.bmj.com/content/75/1/168.full.pdf+html>.

Fukuda et al., The unidirectionality of the labyrinthine reflex in relation to the unidirectionality of the optokinetic reflex. Acta Otolaryngol. Nov.-Dec. 1959;50:507-16.

Garrett et al., EVestG: responses in depressed patients. Conf Proc IEEE Eng Med Biol Soc. 2008;2008:1707-10.

Gordon, Vestibular stimulation in the insane. Mar. 2, 2004. <http://jnnp.bmj.com/content/75/1/168.short/reply#jnnp_el_97>.

Hardesty, Dr. Dizzy's chair may set vertigo sufferers straight. Seattle Times. Jul. 25, 2010.

Jozsvai et al., The effect of autogenic training and biofeedback on motion sickness tolerance. Aviat Space Environ Med. Oct. 1996;67(10):963-8.

McGeoch et al., Behavioural evidence for vestibular stimulation as a treatment for central post-stroke pain. J Neurol Neurosurg Psychiatry. Nov. 2008;79(11):1298-301. doi:10.1136/jnnp.2008.146738. Epub Jun. 11, 2008.

McGeoch et al., Post-stroke tactile allodynia and its modulation by vestibular stimulation: a MEG case study. Acta Neurol Scand. Jun. 2009;119(6):404-9. doi: 10.1111/j.1600-0404.2008.01106.x. Epub Oct. 6, 2008.

Miller et al., Studies of caloric vestibular stimulation: implications for the cognitive neurosciences, the clinical neurosciences and neurophilosophy. Acta Neuropsychiatrica. 2007;19:183-203.

Ngo et al., Caloric vestibular stimulation reveals discrete neural mechanisms for coherence rivalry and eye rivalry: a meta-rivalry model. Vision Res. Sep. 2007;47(21):2685-99. Epub Aug. 24, 2007.

Pettigrew et al., A 'sticky' interhemispheric switch in bipolar disorder? Proc Biol Sci. Nov. 22, 1998;265(1411):2141-8.

Ramachandran et al., Rapid relief of thalamic pain syndrome induced by vestibular caloric stimulation. Neurocase. Jun. 2007;13(3):185-8.

Rine et al., Visual-vestibular habituation and balance training for motion sickness. Phys Ther. Oct. 1999;79(10):949-57.

Sandler et al., Use of Noncontingent Tactile and Vestibular Stimulation in the Treatment of Self-injury: An Interdisciplinary Study. 2007;19:543-55.

Sang et al., Depersonalisation/derealisation symptoms in vestibular disease. J Neurol Neurosurg Psychiatry. Jun. 2006;77(6):760-6. Epub Feb. 7, 2006.

Schiff et al., Does vestibular stimulation activate thalamocortical mechanisms that reintegrate impaired cortical regions? Proc Biol Sci. Feb. 22, 1999;266(1417):421-3.

Soza Ried et al., Asymmetries of vestibular dysfunction in major depression. Neuroscience. Jan. 5, 2007;144(1):128-34. Epub Oct. 30, 2006.

Soza Ried, Right Vestibular Hypo Activity in Depression, the Theory of Suprachiasmatic-Raphe-Vestibular Nuclei System Asymmetry, Chapter 19, pp. 519-538 in Women and Depression, Paula Hernandez and Sara Alonso, editors. Nova Science Publishers;New York: 2009.

Soza Ried, Right Vestibulo-Ocular Reflex Dysfunction in Major Depression. Abstract program of the 16th ASLTBR. 804.

(56) References Cited

OTHER PUBLICATIONS

Tamagni et al., Vestibular Stimulation reduces Unrealistic Optimism. Working paper.

Utz et al., Electrified minds: transcranial direct current stimulation (tDCS) and galvanic vestibular stimulation (GVS) as methods of non-invasive brain stimulation in neuropsychology—a review of current data and future implications. Neuropsychologia. Aug. 2010;48(10):2789-810. doi:10.1016/j.neuropsychologia.2010.06.002. Epub Jun. 11, 2010.

Winter et al., Vestibular stimulation on a motion-simulator impacts on mood States. Front Psychol. 2012;3:499.

Extended European Search Report mailed Sep. 25, 2015 for Application No. EP 13 755 299.8.

International Preliminary Report on Patentability mailed Sep. 12, 2014 for Application No. PCT/IB2013/000871.

Costa, An assessment of optokinetic nystagmus (OKN) in persons with down syndrome. Exp Brain Res. Oct. 2011;214(3):381-91. doi: 10.1007/s00221-011-2834-5. Epub Aug. 14, 2011.

[No Author Listed], Variotherm plus datasheet. ATMOS. Sep. 2008. Retrieved Aug. 2014. <http://cdn.atmosmed.com/docs/1283/it_es_gb_ga_variotisch_2014-08_vers20.odf>.

\* cited by examiner

METHODS, APPARATUSES AND SYSTEMS FOR DIAGNOSIS AND TREATMENT OF MOOD DISORDERS

RELATED APPLICATION

This application claims the benefit under 35 USC §119(e) of U.S. Provisional Application No. 61/604,185, filed Feb. 28, 2012, the disclosure of which is incorporated by reference herein in its entirety.

BACKGROUND

Mood disorders, also called affective disorders, are present in around 10% of the general population at any given time. Depression, the most commonly occurring mood disorder, is characterized by symptoms such as feelings of sadness or emptiness, reduced interest in activities that used to be enjoyed, sleep disturbances, loss of energy, and/or suicidal thoughts or intentions (Diagnosis and Statistical Manual (DSM), 4th Edition, 1994).

It is estimated that, in the United States, around 20% of individuals will suffer from a mood disorder at some time, and that around 16% will suffer a major depressive disorder at some time (Kessler, et al. Arch Gen Psychiatry, 2005; 62:593-602). In the United States, around 3-4% of individuals suffering from depression commit suicide; a population accounting for around 60% of the suicide rate in the country (Barlow D H. Abnormal psychology: An integrative approach (5th ed.)).

Subjects diagnosed with depression are typically treated with a combination of psychotherapy and antidepressant medication, both of which may take a period of months or years to reduce depressive symptoms in the subject. Antidepressant medications also typically have side effects that can make taking the medication unpleasant.

Accordingly, there is a need for a treatment for mood disorders that is easy to administer to a subject, that results in prompt alleviation of symptoms, and that does not result in side effects to the subject.

SUMMARY

The instant disclosure relates to the diagnosis and treatment of mood disorders (e.g., depression). The disclosure also provides systems, apparatuses, and algorithms for use in the diagnosis and treatment of mood disorders (e.g., depression). Diagnosis of a mood disorder (e.g., depression) in a subject (presumably, but not necessarily limited to human subjects as other members of the animal kingdom may be subject to depression and exhibit similar physiology) may be performed via analysis (e.g., measurement) of the subject's response to vestibular stimulation. Right vestibular function in subjects diagnosed with a mood disorder (e.g., depression) is diminished compared with subjects who do not have a mood disorder, and accordingly an analysis (e.g., measurement) of vestibular function in a subject may provide a diagnosis of a mood disorder.

Additionally, treatment of a mood disorder (e.g., depression) in a subject may be performed by applying therapeutic vestibular stimulation to the subject based on an analysis (e.g., measurement) of the right vestibular function in the subject.

According to one aspect of the disclosure, a method of treating a mood disorder in a subject is provided. The method comprises applying diagnostic vestibular stimulation to a subject, registering the subject's response to the diagnostic vestibular stimulation, and applying therapeutic vestibular stimulation to the subject based on the subject's response to the diagnostic vestibular stimulation.

In some embodiments, diagnostic vestibular stimulation and therapeutic vestibular stimulation each comprise applying rotary, caloric or optokinetic stimulation to a subject. The diagnostic vestibular stimulation and/or therapeutic vestibular stimulation may comprise inducing nystagmus in the subject.

In some embodiments, diagnostic vestibular stimulation or therapeutic vestibular stimulation comprise rotary stimulation wherein at least one of: angular acceleration in the range $0.1°/(second)^2$ to $2°/(second)^2$; or angular acceleration in the range $50°/(second)^2$ to $500°/(second)^2$ to bring a subject to rest, is applied to the subject.

In some embodiments, diagnostic vestibular stimulation or therapeutic vestibular stimulation comprise rotary stimulation wherein an angular velocity in the range $50°/second$ to $200°/second$ is applied to a subject.

In some embodiments, diagnostic vestibular stimulation or therapeutic vestibular stimulation comprise caloric stimulation wherein air at a temperature of 49° Celsius is applied to a subject's right ear and/or to the subject's left ear.

In some embodiments, diagnostic vestibular stimulation or therapeutic vestibular stimulation comprise optokinetic stimulation wherein angular acceleration in the range $0.1°/(second)^2$ to $2°/(second)^2$ for a period in the range 1 minute to 3 minutes is applied to a subject.

In some embodiments, diagnostic vestibular stimulation or therapeutic vestibular stimulation comprise optokinetic stimulation, wherein the subject is at rest during optokinetic stimulation and optokinetic stimulation comprises moving visual stimuli.

In some embodiments, registering the subject's response to the diagnostic vestibular stimulation comprises determining a ratio of the slow phase velocity of nystagmus during diagnostic vestibular stimulation to the subject's right side to the slow phase velocity of nystagmus during diagnostic vestibular stimulation to the subject's left side, and applying therapeutic vestibular stimulation to the subject based, at least partly, on said ratio. In some embodiments, the therapeutic vestibular stimulation is based on the age of the subject.

In some embodiments, the mood disorder is depression.

According to another aspect of the disclosure, a system for treating a mood disorder in a subject is provided. The system comprises a processor and a tangible, non-transitory computer recordable and readable medium operatively coupled to the processor, the medium storing computer program instructions which, when executed by the processor, cause the processor to perform a method comprising determining, based on registering the subject's response to diagnostic vestibular stimulation, therapeutic vestibular stimulation to be applied to the subject in order to treat the mood disorder in the subject.

In some embodiments, the diagnostic vestibular stimulation comprises rotary, caloric or optokinetic stimulation. The diagnostic vestibular stimulation depends on the age of the subject.

In some embodiments, the therapeutic vestibular stimulation comprises rotary, caloric or optokinetic stimulation. In some embodiments, the therapeutic vestibular stimulation depends on the age of the subject.

In some embodiments, diagnostic vestibular stimulation or therapeutic vestibular stimulation comprise rotary stimulation wherein at least one of: angular acceleration in the range $0.1°/(second)^2$ to $2°/(second)^2$; or angular acceleration in the range $50°/(\text{second})^2$ to $500°/(\text{second})^2$ to bring a subject to rest, is applied to the subject.

In some embodiments, diagnostic vestibular stimulation or therapeutic vestibular stimulation comprise rotary stimulation wherein an angular velocity in the range $50°/\text{second}$ to $200°/\text{second}$ is applied to a subject.

In some embodiments, diagnostic vestibular stimulation or therapeutic vestibular stimulation comprise caloric stimulation wherein air at a temperature of $49°$ Celsius is applied to a subject's right ear and/or to a subject's left ear.

In some embodiments, diagnostic vestibular stimulation or therapeutic vestibular stimulation comprise optokinetic stimulation wherein angular acceleration in the range $0.1°/(\text{second})^2$ to $2°/(\text{second})^2$ for a period in the range 1 minute to 3 minutes is applied to a subject.

In some embodiments, diagnostic vestibular stimulation or therapeutic vestibular stimulation comprise optokinetic stimulation, wherein the subject is at rest during optokinetic stimulation and optokinetic stimulation comprises moving visual stimuli.

The system may further include means for applying the diagnostic vestibular stimulation to the subject.

In some embodiments, the mood disorder is depression. In some embodiments, the subject is a human subject.

According to yet another aspect of the disclosure, a method of treating a mood disorder in a subject is provided, the method comprises applying therapeutic vestibular stimulation to the subject in order to treat the mood disorder in the subject. In some embodiments, the application of therapeutic vestibular stimulation to the subject depends on the age of the subject.

In some embodiments, therapeutic vestibular stimulation comprises rotary stimulation wherein at least one of: angular acceleration in the range $0.1°/(\text{second})^2$ to $2°/(\text{second})^2$; or angular acceleration in the range $50°/(\text{second})^2$ to $500°/(\text{second})^2$ to bring a subject to rest, is applied to the subject.

In some embodiments, therapeutic vestibular stimulation comprises rotary stimulation wherein an angular velocity in the range $50°/\text{second}$ to $200°/\text{second}$ is applied to a subject.

In some embodiments, therapeutic vestibular stimulation comprises caloric stimulation wherein air at a temperature of $49°$ Celsius is applied to a subject's right ear and/or to the subject's left ear.

In some embodiments, therapeutic vestibular stimulation comprises optokinetic stimulation wherein angular acceleration in the range $0.1°/(\text{second})^2$ to $2°/(\text{second})^2$ for a period in the range 1 minute to 3 minutes is applied to a subject.

In some embodiments, therapeutic vestibular stimulation comprises optokinetic stimulation, wherein the subject is at rest during optokinetic stimulation and optokinetic stimulation comprises moving visual stimuli.

In some embodiments, applying the therapeutic vestibular stimulation to the subject is based on a ratio of the slow phase velocity of nystagmus on the subject's right side to the slow phase velocity of nystagmus on the subject's left side.

In some embodiments, the mood disorder is depression. In some embodiments, the subject is a human subject.

According to still another aspect of the disclosure, a method of treating a mood disorder in a subject is provided. The method comprises obtaining data for performing therapeutic vestibular stimulation of a subject, and applying therapeutic vestibular stimulation to the subject based on the data in order to treat the mood disorder in the subject.

In some embodiments, the therapeutic vestibular stimulation applied to the subject comprises rotary, caloric or optokinetic stimulation.

In some embodiments, therapeutic vestibular stimulation comprises rotary stimulation wherein at least one of: angular acceleration in the range $0.1°/(\text{second})^2$ to $2°/(\text{second})^2$; or angular acceleration in the range $50°/(\text{second})^2$ to $500°/(\text{second})^2$ to bring a subject to rest, is applied to the subject.

In some embodiments, therapeutic vestibular stimulation comprises rotary stimulation wherein an angular velocity in the range $50°/\text{second}$ to $200°/\text{second}$ is applied to a subject.

In some embodiments, therapeutic vestibular stimulation comprises caloric stimulation wherein air at a temperature of $49°$ Celsius is applied to a subject's right ear and/or to the subject's left ear.

In some embodiments, therapeutic vestibular stimulation comprises optokinetic stimulation wherein angular acceleration in the range $0.1°/(\text{second})^2$ to $2°/(\text{second})^2$ for a period in the range 1 minute to 3 minutes is applied to a subject.

In some embodiments, therapeutic vestibular stimulation comprises optokinetic stimulation, wherein the subject is at rest during optokinetic stimulation and optokinetic stimulation comprises moving visual stimuli.

In some embodiments, the data comprises an indication of a ratio of the slow phase velocity of nystagmus on the subject's right side to the slow phase velocity of nystagmus on the subject's left side.

In some preferred embodiments, the mood disorder is depression. In some embodiments, the subject is a human subject.

According to another aspect of the disclosure, an apparatus for treating a mood disorder in a subject is provided. The apparatus comprises one or more devices for applying therapeutic vestibular stimulation to the subject, an interface for automatically operating said one or more devices, a processor and at least one computer readable medium encoded with a program that, when executed by the processor, performs a therapeutic method, the method comprising: obtaining data for performing therapeutic vestibular stimulation to the subject, and via the interface, applying therapeutic vestibular stimulation to the subject based on the data in order to treat the mood disorder in the subject.

In some embodiments, therapeutic vestibular stimulation comprises rotary stimulation wherein at least one of: angular acceleration in the range $0.1°/(\text{second})^2$ to $2°/(\text{second})^2$; or angular acceleration in the range $50°/(\text{second})^2$ to $500°/(\text{second})^2$ to bring a subject to rest, is applied to the subject.

In some embodiments, therapeutic vestibular stimulation comprises rotary stimulation wherein an angular velocity in the range $50°/\text{second}$ to $200°/\text{second}$ is applied to a subject.

In some embodiments, therapeutic vestibular stimulation comprises caloric stimulation wherein air at a temperature of $49°$ Celsius is applied to a subject's right ear and/or to the subject's left ear.

In some embodiments, therapeutic vestibular stimulation comprises optokinetic stimulation wherein angular acceleration in the range $0.1°/(\text{second})^2$ to $2°/(\text{second})^2$ for a period in the range 1 minute to 3 minutes is applied to a subject.

In some embodiments, therapeutic vestibular stimulation comprises optokinetic stimulation, wherein the subject is at rest during optokinetic stimulation and optokinetic stimulation comprises moving visual stimuli.

In some embodiments, the data for performing therapeutic vestibular stimulation to the subject comprises an indication of a ratio of the slow phase velocity of nystagmus on the subject's right side to the slow phase velocity of nystagmus on the subject's left side.

In some embodiments, the mood disorder is depression. In some embodiments, the subject is a human subject.

According to another aspect of the disclosure, a computer readable medium encoded with a program that, when executed, causes a suitable apparatus to perform a therapeutic method. The method comprises applying therapeutic vestibular stimulation to a subject in order to treat a mood disorder in the subject.

In some embodiments, therapeutic vestibular stimulation comprises rotary stimulation wherein at least one of: angular acceleration in the range $0.1°/(second)^2$ to $2°/(second)^2$; or angular acceleration in the range $50°/(second)^2$ to $500°/(second)^2$ to bring a subject to rest, is applied to the subject.

In some embodiments, therapeutic vestibular stimulation comprises rotary stimulation wherein an angular velocity in the range 50°/second to 200°/second is applied to a subject.

In some embodiments, therapeutic vestibular stimulation comprises caloric stimulation wherein air at a temperature of 49° Celsius is applied to a subject's right ear and/or to the subject's left ear.

In some embodiments, therapeutic vestibular stimulation comprises optokinetic stimulation wherein angular acceleration in the range $0.1°/(second)^2$ to $2°/(second)^2$ for a period in the range 1 minute to 3 minutes is applied to a subject.

In some embodiments, therapeutic vestibular stimulation comprises optokinetic stimulation, wherein the subject is at rest during optokinetic stimulation and optokinetic stimulation comprises moving visual stimuli.

In some embodiments, applying therapeutic vestibular stimulation to the subject is based on the ratio of the slow phase velocity of nystagmus on the subject's right side to the slow phase velocity of nystagmus on the subject's left side. In some embodiments, applying therapeutic vestibular stimulation to the subject is based on the age of the subject.

In some embodiments, the mood disorder is depression. In some embodiments, the subject is a human subject.

According to still another aspect of the disclosure, an apparatus for diagnosing a mood disorder in a subject is provided. The apparatus comprises a mechanism that applies diagnostic vestibular stimulation to the subject, a mechanism for registering the subject's response to the diagnostic vestibular stimulation, and at least one computer readable medium encoded with a program that, when executed, performs a diagnostic method, comprising registering the subject's response to the diagnostic vestibular stimulation.

In some embodiments, the subject is identified as having a mood disorder based on the subject's response to the diagnostic vestibular stimulation.

In some embodiments, the diagnostic vestibular stimulation comprises applying rotary, caloric or optokinetic stimulation. The diagnostic vestibular stimulation may comprise inducing nystagmus in the subject.

In some embodiments, diagnostic vestibular stimulation comprises rotary stimulation wherein at least one of: angular acceleration in the range $0.1°/(second)^2$ to $2°/(second)^2$; or angular acceleration in the range $50°/(second)^2$ to $500°/(second)^2$ to bring a subject to rest, is applied to the subject.

In some embodiments, diagnostic vestibular stimulation comprises rotary stimulation wherein an angular velocity in the range 50°/second to 200°/second is applied to a subject.

In some embodiments, diagnostic vestibular stimulation comprises caloric stimulation wherein air at a temperature of 49° Celsius is applied to a subject's right ear and/or to the subject's left ear.

In some embodiments, diagnostic vestibular stimulation comprises optokinetic stimulation wherein angular acceleration in the range $0.1°/(second)^2$ to $2°/(second)^2$ for a period in the range 1 minute to 3 minutes is applied to a subject.

In some embodiments, diagnostic vestibular stimulation comprises optokinetic stimulation, wherein the subject is at rest during optokinetic stimulation and optokinetic stimulation comprises moving visual stimuli.

In some embodiments, registering the subject's response to the diagnostic vestibular stimulation comprises determining a ratio of the slow phase velocity of nystagmus on the subject's right side to the slow phase velocity of nystagmus on the subject's left side.

In some embodiments, the mood disorder is depression. In some embodiments, the subject is a human subject.

According to yet another aspect of the disclosure, a tangible, non-transitory computer readable medium encoded with a program that, when executed causes a suitable apparatus to perform a diagnostic method. The diagnostic method comprises registering a subject's response to diagnostic vestibular stimulation applied to the subject. In some embodiments, the subject is identified as having a mood disorder based on the subject's response to the diagnostic vestibular stimulation.

The diagnostic vestibular stimulation applied to the subject may be applied via rotary, caloric or optokinetic stimulation. In some embodiments, the diagnostic vestibular stimulation applied to the subject comprises inducing nystagmus in the subject.

In some embodiments, diagnostic vestibular stimulation comprises rotary stimulation wherein at least one of: angular acceleration in the range $0.1°/(second)^2$ to $2°/(second)^2$; or angular acceleration in the range $50°/(second)^2$ to $500°/(second)^2$ to bring a subject to rest, is applied to the subject.

In some embodiments, diagnostic vestibular stimulation comprises rotary stimulation wherein an angular velocity in the range 50°/second to 200°/second is applied to a subject.

In some embodiments, diagnostic vestibular stimulation comprises caloric stimulation wherein air at a temperature of 49° Celsius is applied to a subject's right ear and/or to the subject's left ear.

In some embodiments, diagnostic vestibular stimulation comprises optokinetic stimulation wherein angular acceleration in the range $0.1°/(second)^2$ to $2°/(second)^2$ for a period in the range 1 minute to 3 minutes is applied to a subject.

In some embodiments, diagnostic vestibular stimulation comprises optokinetic stimulation, wherein the subject is at rest during optokinetic stimulation and optokinetic stimulation comprises moving visual stimuli.

In some embodiments, registering the subject's response to diagnostic vestibular stimulation comprises determining a ratio of the slow phase velocity of nystagmus on the subject's right side to the slow phase velocity of nystagmus on the subject's left side.

In some embodiments, the mood disorder is depression. In some embodiments, the subject is a human subject.

According to yet another aspect of the disclosure, a method of preventing a mood disorder in a subject is provided. The method comprises applying therapeutic vestibular stimulation to a subject known to prevent or reduce the severity of the mood disorder if it were to occur.

The therapeutic vestibular stimulation applied to the subject may be applied via rotary, caloric or optokinetic stimulation. In some embodiments, the therapeutic vestibular stimulation applied to the subject comprises inducing nystagmus in the subject.

In some embodiments, therapeutic vestibular stimulation comprises rotary stimulation wherein at least one of: angular acceleration in the range $0.1°/(second)^2$ to $2°/(second)^2$; or angular acceleration in the range $50°/(second)^2$ to $500°/(second)^2$ to bring a subject to rest, is applied to the subject.

In some embodiments, therapeutic vestibular stimulation comprises rotary stimulation wherein an angular velocity in the range 50°/second to 200°/second is applied to a subject.

In some embodiments, therapeutic vestibular stimulation comprises caloric stimulation wherein air at a temperature of 49° Celsius is applied to a subject's right ear and/or to the subject's left ear.

In some embodiments, therapeutic vestibular stimulation comprises optokinetic stimulation wherein angular acceleration in the range $0.1°/(second)^2$ to $2°/(second)^2$ for a period in the range 1 minute to 3 minutes is applied to a subject.

In some embodiments, therapeutic vestibular stimulation comprises optokinetic stimulation, wherein the subject is at rest during optokinetic stimulation and optokinetic stimulation comprises moving visual stimuli.

In some embodiments, therapeutic vestibular stimulation is based on a ratio of the slow phase velocity of nystagmus on the subject's right side to the slow phase velocity of nystagmus on the subject's left side.

In some embodiments, treating a mood disorder comprises one or more treatment sessions occurring approximately one week apart.

In some embodiments, the mood disorder is depression. In some embodiments, the subject is a human subject.

The foregoing is a non-limiting summary of the disclosure. These and other aspects of the disclosure, as well as various advantages and utilities will be apparent with reference to the Detailed Description. Each aspect of the disclosure can encompass various embodiments as will be understood.

All documents identified in this disclosure are incorporated in their entirety herein by reference.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
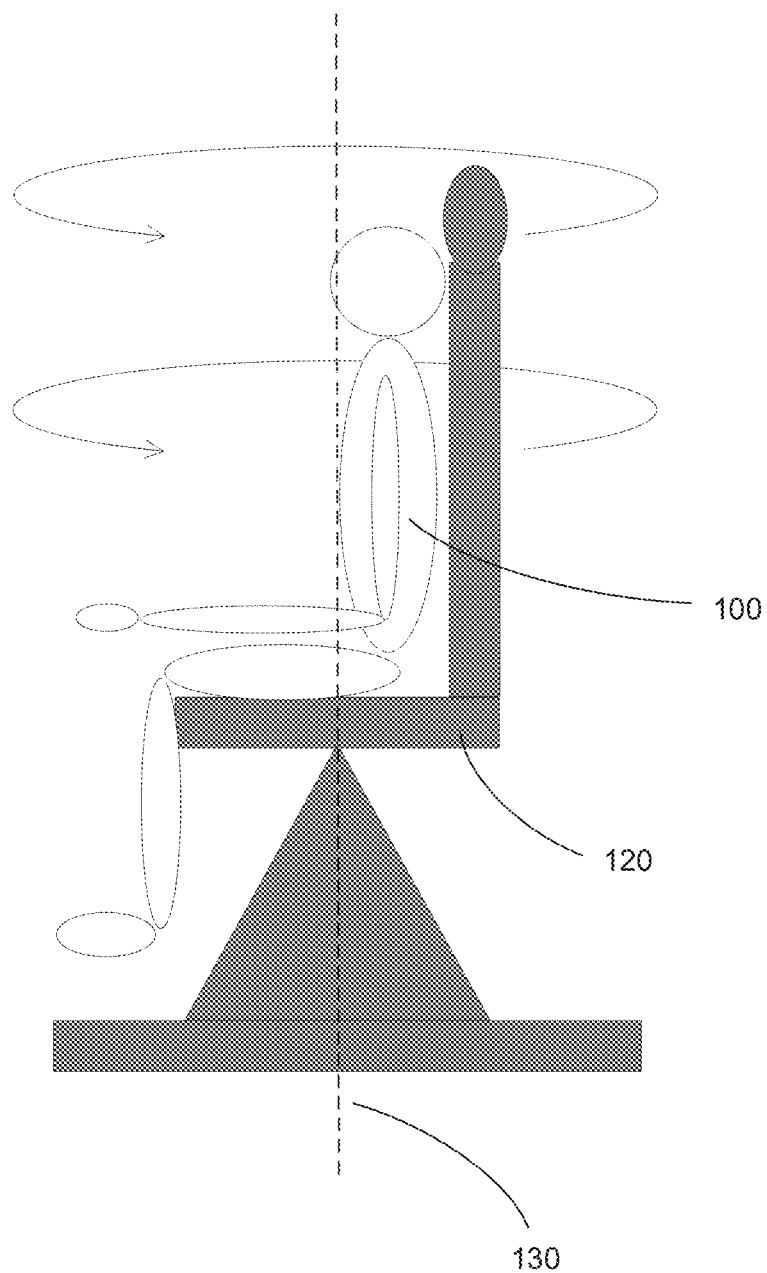
FIG. 1 is a schematic depicting the application of rotational vestibular stimulation to a subject, according to some embodiments.

Mood disorders, which are present in around 10% of the general population at any given time, are currently treated via a combination of antidepressant medications, that can have secondary non-beneficial effects ("side effects") and are expensive, and by psychotherapy. Both approaches may take months or years to alleviate symptoms, and may not work at all for some subjects. As a result, subjects frequently experience side effects caused by antidepressant medications for long periods of time. The time for subjects to respond to these therapies is critically important in light of, among other factors, the dramatically increased suicide rate for subjects suffering with a mood disorder compared with healthy subjects (e.g., subjects not suffering with a mood disorder).

The inventor has recognized and appreciated that stimulation of the vestibular system of a subject may be applied to treat a mood disorder in the subject. A depressed subject may show an abnormal response to vestibular stimulation compared to a non-depressed subject, and stimulation of the vestibular system of the depressed subject may ameliorate the subject's symptoms of depression. In addition, the inventor has recognized and appreciated that the right side of a depressed subject's vestibular system is less active than the left side, and a measurement of the difference may be used to diagnose and/or treat symptoms of depression in the subject.

The present disclosure is directed to the diagnosis and treatment of mood disorders. The Diagnostic and Statistical Manual, 4th edition (DSM-IV) describes mood disorders as: "those where the primary symptom is a disturbance in mood. In other words, inappropriate, exaggerated, or limited range of feelings. Everybody gets down sometimes, and everybody experiences a sense of excitement and emotional pleasure. To be diagnosed with a mood disorder, your feelings must be to the extreme. In other words, crying, and/or feeling depressed, suicidal frequently. Or, the opposite extreme, having excessive energy where sleep is not needed for days at a time and during this time the decision making process is significantly hindered."

The DSM-IV categorizes four primary types of disorders as mood disorders: Bipolar Disorder, Cyclothymic Disorder, Dysthymic Disorder and Major Depressive Disorder. The present disclosure may be applied to these and any other mood disorder, including Mixed Anxiety/Depression, Disruptive Mood Dysregulation Disorder, Grief, and Premenstrual Dysphoric Disorder, currently proposed for inclusion in the forthcoming Diagnostic and Statistical Manual, $5^{th}$ edition (DSM-V). Furthermore, the present disclosure may be applied to the diagnosis and/or treatment of mood episodes, such as manic or hypomanic episodes.

In some embodiments, Major Depressive Disorder, also known as depression, is diagnosed and/or treated. Depression may be defined via the DSM-IV description of the symptoms of Major Depressive Disorder:

depressed mood (such as feelings of sadness or emptiness);

reduced interest in activities that used to be enjoyed;

sleep disturbances (either not being able to sleep well or sleeping to much);

loss of energy or a significant reduction in energy level;

difficulty concentrating, holding a conversation, paying attention, or making decisions that used to be made fairly easily; and suicidal thoughts or intentions.

In other embodiments, depression is defined by a score assessed via a questionnaire, such as the Hamilton Depression Scale Rating (HAM-D), or the Beck Depression Inventory (BDI). However, any suitable definition of depression may be used to identify subjects as experiencing symptoms of depression. In some embodiments, subjects suffering from depression may be identified by a psychiatrist, psychologist, or other mental health professional.

The treatment of a mood disorder in a subject may comprise any process after which the symptoms of the disorder in the subject are ameliorated, for any length of time. For example, a depressed subject may report an improved mood or a reduction in suicidal thoughts immediately after treatment. A subject may also report a change in symptoms a period of hours, days or weeks after treatment. In some embodiments, treatment is preventative/prophylactic in nature, such that treatment of a subject is applied in order to prevent symptoms of a mood disorder from appearing, from increasing in magnitude or duration, or from occurring at all.

In some embodiments, the subject is an individual who has previously been diagnosed with a mood disorder. As used herein, a subject includes a mammal, such as a human, non-human primate, cow, rabbit, horse, pig, sheep, goat, dog, cat, or rodent such a rat, mouse or a rabbit. In some embodiments, the subject is a human. Diagnosis may be performed via any suitable method, including those described above. In some embodiments, a subject is diagnosed and/or treated for a mood disorder by applying certain embodiments of the instant disclosure.

In some embodiments, the method or means of diagnosing a subject with a mood disorder and/or treating a subject for a mood disorder is based on the age of the subject. For example, the subject's age may be a parameter used to determine precisely how to implement treatment. Other attributes associated with a subject may also determine in part how diagnostic and/or therapeutic methods are to be applied. Such attributes may include gender, height, weight, and medical condition, although any parameter that is particular to an individual subject may be used.

In some embodiments, vestibular stimulation is applied to a subject. Vestibular stimulation may comprise actions applied to a subject that excite the vestibulo-ocular reflex in the subject. Vestibular stimulation may be applied via any suitable method, including rotary (body-head acceleration) stimulation, optokinetic stimulation, caloric stimulation and galvanic stimulation. Such stimulation may be applied in order to diagnose and/or treat a mood disorder in a subject.

The vestibulo-ocular reflex is a reflex eye movement that stabilizes images on the retina during head movement by producing an eye movement in the direction opposite to the head movement, thus preserving the location of the image in the visual field. The vestibulo-ocular reflex is driven by signals from a vestibular apparatus located within the inner ear.

FIG. 1 shows an example of applying vestibular stimulation to a subject in the form of rotary stimulation. In the example of FIG. 1, subject 100 sits in rotary chair 120 that rotates around axis 130. The axis of rotation may be situated in any location such that rotating the chair excites the subject's vestibulo-ocular reflex. There is no requirement that the subject be seated on a chair, and the subject may instead be situated on a rotating platform or on any suitable device which, through movement of the subject, stimulates the subject's vestibulo-ocular reflex.

A rotary chair used for applying vestibular stimulation to a subject may be any suitable chair that can be rotated freely, though may comprise a commercially available rotary chair such as the Nydiag 200 Rotary Chair sold by Interacoustics® or the I-Portal® NOTC system sold by Neuro Kinetics, Inc.

In some embodiments, a rotary chair used to provide rotary vestibular stimulation to a subject is controlled automatically by a computing device. Such as configuration may allow a computing device to be programmed to perform a sequence of actions via a rotary chair. For example, a computing device may be programmed to accelerate a chair at a fixed acceleration for a length of time then moved at a fixed velocity, then be brought to rest.

In the example of FIG. 1, subject 100 may be rotated in rotary chair 120 at a fixed velocity, for example at a rotational frequency between 0.001 Hz and 1.5 Hz (corresponding to angular velocities of 0.36°/second and 540°/second, respectively). A subject may also be rotated with a velocity that increases or decreases over time; for example, by an angular acceleration between $\pm 0.1°/(second)^2$ and $\pm 200°/(second)^2$.

In some embodiments, measurements of the subject's vestibulo-ocular reflex as a result of rotational stimulation of the vestibular system are performed. Such measurements may be performed while the subject is in motion, or while the subject is at rest; for example, immediately after coming to rest.

In some embodiments, a subject's vestibular system is stimulated via caloric stimulation. In some embodiments, caloric stimulation comprises irrigating cold or warm water, or cold or warm air, into the external auditory canal (ear canal) of a subject in order to stimulate the vestibular system. This may be achieved, for example, via a syringe, via the insertion of fluid capillaries, and/or via an air delivery system placed near or within the ear canal. When water or air is introduced into the ear canal, it may stimulate or inhibit signals from the vestibular apparatus in the brain, depending upon the temperature of the water or air. In some use cases, water at a temperature below body temperature, and preferably at a temperature of approximately 30° Celsius, may be used to inhibit signals from the vestibular apparatus. In some use cases, water at a temperature above body temperature, and preferably at a temperature of approximately 44° Celsius, may be used to stimulate signals from the vestibular apparatus.

Caloric stimulation may be applied to either the right ear canal or the left ear canal in a subject at one time, or to both ear canals at the same time, in order to stimulate the right and/or left side of the subject's vestibular system. Any suitable material other than water may be used to stimulate or inhibit signals from the vestibular apparatus in a subject. Hot or cold air, for example, may be applied for this purpose. Such stimulation may be applied in order to diagnose and/or treat a mood disorder in a subject.

A caloric device used for applying vestibular stimulation to a subject may be any suitable device that can apply a temperature above or below the subject's body temperature to the subject's ear canal, though may comprise a commercially available caloric stimulation system such as the ICS NCA-200 or Hortmann Airmatic II models sold by Otometrics.

In some embodiments, optokinetic stimulation is used to stimulate a subject's vestibular system. Optokinetic stimulation comprises presenting a subject with a visual stimulus that is moving with respect to the subject. For example, a visual stimulus may be at rest and the subject may be rotating (e.g., on chair 120 shown in FIG. 1). The visual stimulus may also rotate around the subject while the subject is at rest.

Figure 2:
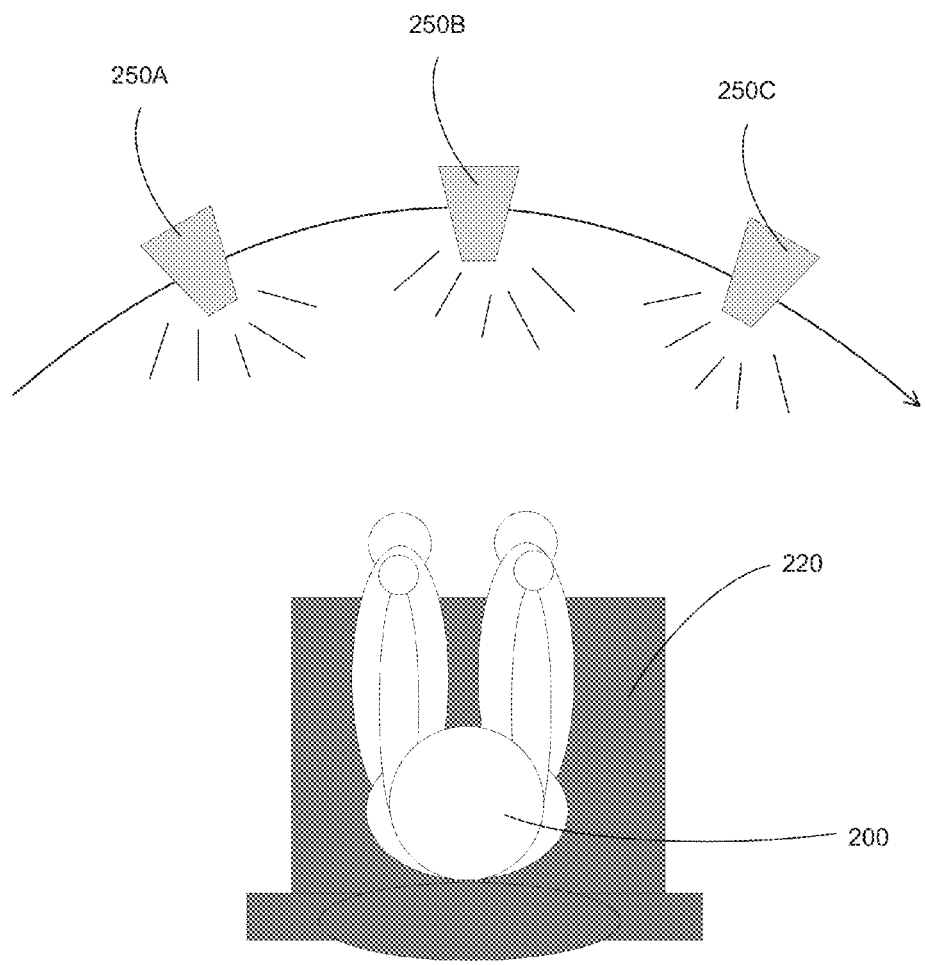
FIG. 2 is a schematic depicting the application of optokinetic vestibular stimulation to a subject, according to some embodiments.

FIG. 2 shows an example of applying optokinetic stimulation to a subject 200. The view depicted in FIG. 2 is situated directly above the subject, looking down. Strips of light 250A-C rotate around the subject in a circle, causing the subject to follow the strips of light with his eyes. As noted above, an alternative configuration would be for the subject to rotate in chair 220 while the strips of light 250A-C remain stationary.

In some embodiments, optokinetic stimulation may be applied using an optokinetic drum, comprising a series of vertical stripes that move relative to a subject's eyes. Optokinetic stimulation may also be applied using one or more dots of light that move relative to the subject. However, any suitable method of providing optokinetic stimulation may be used. Such stimulation may be applied in order to diagnose and/or treat a mood disorder in a subject.

The above-described methods of stimulating a subject's vestibular system are provided as examples only, and the disclosure is not limited to a particular method of stimulating a subject's vestibular system in order to diagnose and/or treat a mood disorder in the subject.

In some embodiments, the subject's response to one or more methods of stimulating the subject's vestibular system is measured. The form of such a measurement will depend both upon the method of vestibular stimulation being applied in addition to the type of response exhibited by a subject.

The stimulation of the vestibular system of a subject may result in the subject experiencing involuntary movements associated with the vestibulo-ocular reflex. The subject may experience involuntary movement of the eyes, known as nystagmus (specifically physiologic nystagmus, being nystagmus induced via the vestibulo-ocular reflex).

Nystagmus is characterized by a series of alternating slow and fast eye movements. For example, as a subject's eyes track a series of vertical stripes, as in a case where optokinetic stimulation is used to induce nystagmus, the eyes will tend to fixate on a single stripe, to slowly follow it, then quickly jump to another stripe. Nystagmus comprises a slow phase, for example, during fixation on a stripe in the above example; and a fast phase, for example during a quick jump to another strip in the above example.

Figure 3:
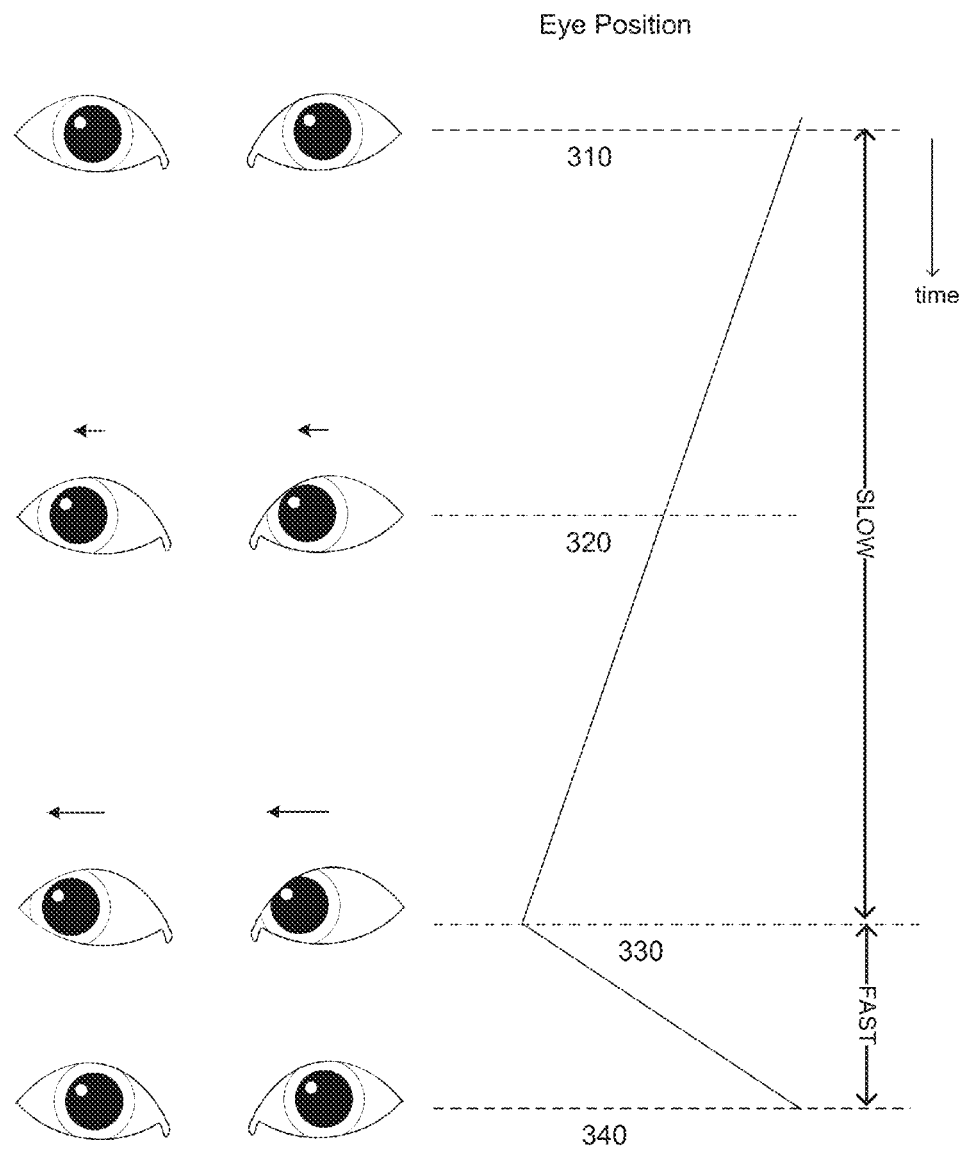
FIG. 3 depicts the changing position of the eyes during nystagmus.

FIG. 3 shows an example of the changing position of the eyes during nystagmus. Time increases moving down the page such that step 310 exhibits the beginning of a cycle of nystagmus and step 340 exhibits the end. At step 310 the eyes point forward, roughly in the center of the visual field. At step 320, the eyes have moved to the left (subject's right) as a result of the vestibulo-ocular reflex reacting to stimulation of the vestibular system. In the example of FIG. 3, this vestibular stimulation may comprise any suitable form of stimulation.

At step 330 the eyes have moved further to the left, and at step 340 the eyes have moved back to a forward-facing position. The slow phase of nystagmus comprises the time between step 310 and step 330, during which the eyes slowly move to one side of the subject. The fast phase of nystagmus comprises the time between step 330 and step 340, during which the eyes quickly transition to a position roughly in the center of the visual field. The fast phase of nystagmus is typically much shorter than the slow phase of nystagmus.

After step 340, the process may begin again at step 310, depending upon the type of vestibular stimulation being applied.

The above description of nystagmus applies to any form of vestibular stimulation that triggers the vestibulo-ocular reflex, including rotary, caloric and optokinetic stimulation of the vestibular system. To illustrate the ways in which nystagmus occurs as a result of these types of vestibular stimulation, we describe some specific manifestations below.

During rotary stimulation, nystagmus may occur while the subject is rotating, with the slow phase of nystagmus occurring in a direction opposite to rotation and the fast phase of nystagmus being with the direction of rotation. Nystagmus may occur in this way independent of any visual stimuli, i.e., nystagmus may occur in a subject who is rotating in the dark. In addition, if the rotation of a subject is made to stop suddenly, additional nystagmus may occur. Rotary stimulation may be used to test both the right and left vestibular systems, because both are stimulated by the rotation.

Caloric stimulation may be used to stimulate each of the left and/or right vestibular systems by applying caloric stimulation to a single ear at a time. The direction of nystagmus (i.e., to the subject's right or left side) depends upon which ear is being stimulated and of the temperature of the water or air being used to perform caloric stimulation. For stimulation below body temperature, the direction of the fast phase of nystagmus is towards the contralateral ear; that is, the ear not experiencing caloric stimulation. For stimulation above body temperature, the direction of the fast phase of nystagmus is towards the ipsilateral ear; that is, the ear that is experiencing caloric stimulation.

For optokinetic stimulation, the slow phase of nystagmus may occur when the subject is tracking a pattern (such as a vertical stripe) or light is being used to provide optokinetic stimulation. The eyes make a quick movement to catch up with the next pattern or light, resulting in the nystagmus pattern. The direction of the fast phase of nystagmus is accordingly in a direction opposite to that of the relative motion of the subject with respect to the optokinetic stimulation.

In some embodiments, a subject's response to vestibular stimulation is measured, for example by monitoring the subject's eyes during nystagmus. Such measurements may be used to diagnose and/or treat the subject based on the subject's response to the vestibular stimulation.

Figure 4A:
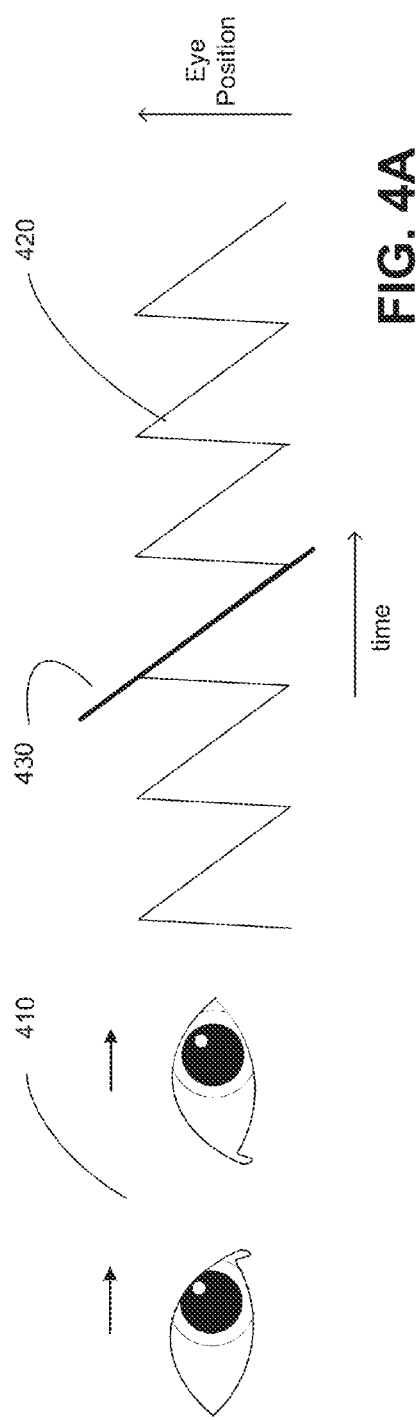
FIG. 4A depicts the position of the eyes during nystagmus to the left side and portrays a calculation of the slow phase velocity, according to some embodiments.
Figure 4B:
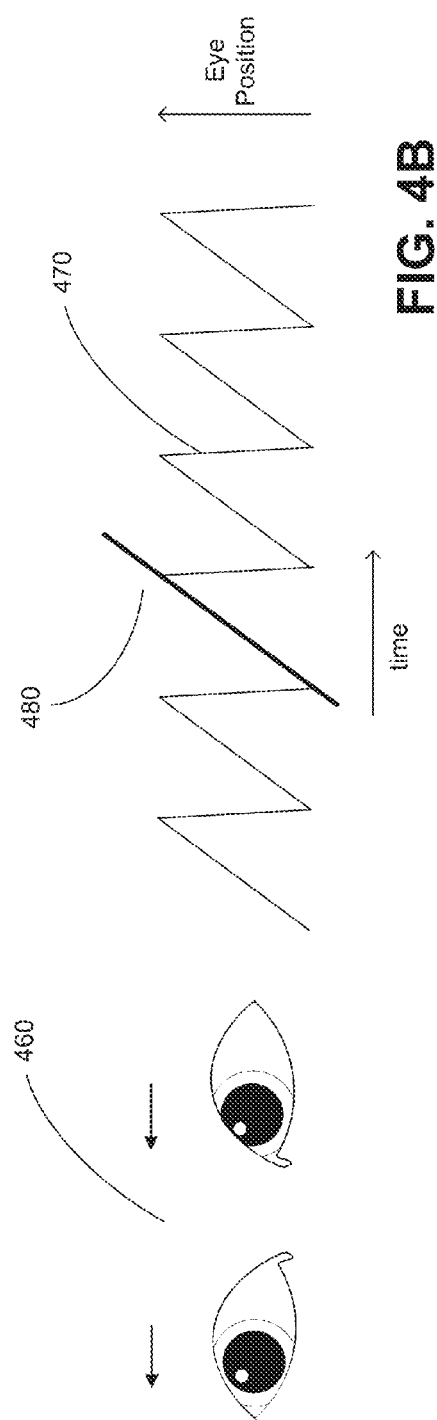
FIG. 4B depicts the position of the eyes during nystagmus to the right side and portrays a calculation of the slow phase velocity, according to some embodiments.

In further embodiments, the response of a subject to vestibular stimulation comprises nystagmus, and the nystagmus of the subject is measured. FIGS. 4A and 4B show illustrative examples of measuring one attribute of a subject's nystagmus. FIG. 4A depicts a nystagmus in which the subject's eyes 410 move to the right (subject's left) during the slow phase of nystagmus and back to the center of the subject's visual field at the end of the fast phase of nystagmus. Chart 420 shows the eye position of the subject over time for an example response in which the subject's eyes repeatedly experience slow and fast phases of nystagmus, wherein the slow phase of nystagmus occurs to the subject's left side.

By tracking the subject's eyes over time during nystagmus, the speed and pattern of nystagmus may be measured. For example, the slow phase velocity, being the velocity at which the subject's eyes move during the slow phase of nystagmus, may be measured. The slow phase velocity is depicted in FIG. 4A via the slope of line 430, that may be measured in order to determine the slow phase velocity.

FIG. 4B similarly depicts nystagmus in which the subject's eyes 460 move to the left (subject's right) during the slow phase of nystagmus and back to the center of the subject's visual field at the end of the fast phase of nystagmus. Chart 470 shows the eye position of the subject over time for an example response in which the subject's eyes repeatedly experience slow and fast phases of nystagmus, wherein the slow phase of nystagmus occurs to the subject's right side. The slow phase velocity is depicted in FIG. 4B via the slope of line 480, that may be measured in order to determine the slow phase velocity.

It will be appreciated by those skilled in the art that FIGS. 4A and 4B provide idealized depictions of nystagmus of a subject, and that in general the nystagmus pattern of a subject may be less regular than depicted. Accordingly, computerized methods of calculating attributes of a subject's nystagmus, such as the slow phase velocity of nystagmus, may be applied.

In some embodiments, the slow phase velocity of nystagmus of a subject is measured during vestibular stimulation of one side of the subject; for example, by applying caloric stimulation to the ear on that side of the subject. In further embodiments, the slow phase velocity of nystagmus on the subject's right side and the slow phase velocity of nystagmus on the subject's left side are each measured. These measurements may be compared, for example, by calculating a ratio of the slow phase velocity of nystagmus on the subject's right side to the slow phase velocity of nystagmus on the subject's left side.

In other embodiments, other facets of a subject's nystagmus may be measured. For example, an appropriate time series or time-frequency analysis may be applied to the measurement of a subject's nystagmus in order to determine diagnostic and/or therapeutic methods of treating a mood disorder. Thus events such as dysrhythmic nystagmus may be identified and quantified.

Figure 5A:
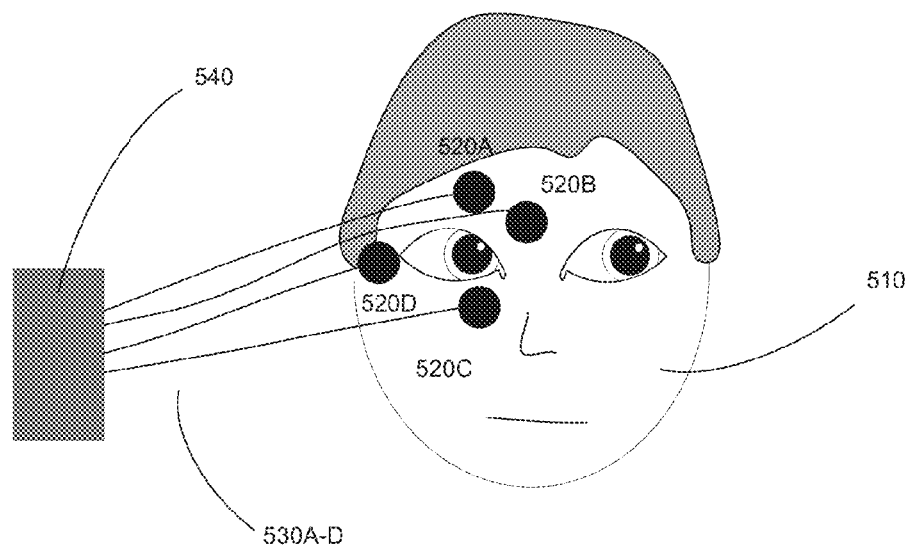
FIG. 5A depicts an example of measuring nystagmus in a subject using electronystagmography.
Figure 5B:
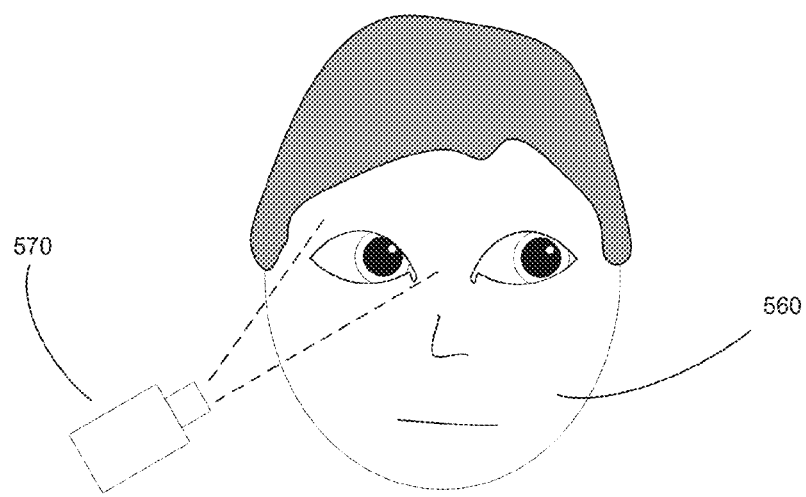
FIG. 5B depicts an example of measuring nystagmus in a subject using videonystagmography.

Registering a subject's response to vestibular stimulation may be performed in any suitable way. FIGS. 5A and 5B depict illustrative methods of measuring nystagmus in a subject. FIG. 5A depicts an example of electronystagmography, wherein electrodes 520A-D are attached around the nose and eye of a subject 510 using conducting gel, and which measure movements of the subject's eye. Data from electrodes 520A-D are transmitted via connectors 530A-D to station 540, which is a computing device used to capture and/or analyze data from the electrodes. However, any number of electrodes, and any configuration of electrodes and computerized devices, may be used such that the movement of a subject's eyes are registered.

FIG. 5B depicts an example of videonystagmography, wherein a camera is used to monitor the motion of a subject's eyes during nystagmus. The camera may comprise any suitable form, including the form of goggles worn over the face of a subject. The camera may also capture images in visible as well as non-visible light, such as infrared light.

It will be understood by those of skill in the art that methods of registering a subject's response to vestibular stimulation, and in particular methods of registering a subject's nystagmus, are not limited to those described above, and that any suitable method may be employed.

Diagnosis of a Mood Disorder

The inventor has recognized and appreciated that right vestibular function is diminished compared with left vestibular function in subjects diagnosed with depression, whereas subjects who are not depressed have approximately symmetric vestibular activity. For example, the slow phase velocity of nystagmus on the right side of a depressed subject may be lower than for a subject who is not depressed.

In some embodiments, a mood disorder is diagnosed in a subject via diagnostic vestibular stimulation. Diagnostic vestibular stimulation may comprise any one or more methods of vestibular stimulation, applied in any way. For example, diagnostic vestibular stimulation may comprise one or more of rotary, caloric and/or optokinetic stimulation. Furthermore, diagnostic vestibular stimulation may comprise vestibular stimulation that stimulates the right, left, or both sides of the vestibular system of a subject.

In some embodiments, diagnostic vestibular stimulation comprises rotary stimulation wherein an accelerating rotation of approximately $25°/second^2$ for approximately 4 seconds is applied to a subject, after which the subject is brought quickly to rest, for example over 1 second or less via a deceleration of $-100°/second^2$ or greater. The nystagmus of the subject may be measured during acceleration and/or deceleration, via any suitable method, including via electronystagmography. Accelerating rotation followed by a decelerating rotation may be performed toward the subject's right and/or left side, in either order, to stimulate the left and right sides of the subject's vestibular system, respectively.

In some embodiments, a subject may be given simple mental tasks, such as basic mathematical problems, to perform while rotary stimulation is applied. This may be performed to, for example, ensure the alertness of the subject. However, any non-interfering method of ensuring the subject is alert during rotary stimulation in order to ensure a suitable quality of measurement data may be used.

In some embodiments, measurements of the nystagmus of a subject during acceleration/deceleration may be used to calculate the slow phase velocity of nystagmus of the subject. In some embodiments, such rotary stimulation is used to calculate the ratio of the slow phase velocity of nystagmus on the subject's right side to the slow phase velocity of nystagmus on the subject's left side.

In further embodiments, the above ratio may be used to perform a diagnosis of a mood disorder. As a non-limiting example, a ratio of the slow phase velocity of nystagmus on the subject's right side to the slow phase velocity of nystagmus on the subject's left side below approximately 1.0 may be used to indicate diagnosis of a mood disorder. Instead of, or in addition to, the above non-limiting example, a ratio of the slow phase velocity of nystagmus on the subject's right side to the slow phase velocity of nystagmus on the subject's left side of approximately 1.1 or greater may be used to indicate a healthy subject.

Those of skill in the art will appreciate that the above values are provided as examples, and that any method of measuring the diminished function of a subject's right vestibular system compared with the subject's left vestibular function, may be used. For example, the difference between the slow phase velocity of nystagmus on the subject's right side and the slow phase velocity of nystagmus on the subject's left side may be used to diagnose a mood disorder in a subject. In general, however, any combination of measurements of a subject which comprise measurements of the function of the subject's vestibular system may be used to diagnose a mood disorder in the subject.

Diagnosis of a mood disorder may be performed on a subject of any age, but preferably on a subject with an age between about 16 and 90 years.

Treatment of a Mood Disorder

The inventor has recognized and appreciated that therapeutic vestibular stimulation may be applied to a subject with a mood disorder in order to treat the mood disorder in the subject. Therapeutic vestibular stimulation may comprise any one or more methods of vestibular stimulation, applied in any way. For example, therapeutic vestibular stimulation may comprise one or more of rotary, caloric and/or optokinetic stimulation. Therapeutic vestibular stimulation may comprise vestibular stimulation that stimulates the right, left, or both sides of the vestibular system of a subject.

In some embodiments, therapeutic vestibular stimulation comprises rotary stimulation. In further embodiments, the therapeutic vestibular stimulation comprises rotary stimulation to the left side of the subject. The rotary stimulation may comprise a constant angular velocity, for example between 1°/second and 200°/second, or may comprise a constant angular acceleration, for example between 0.1°/second$^2$ and 2°/second$^2$. In some embodiments, an angular acceleration of approximately 1°/second$^2$ is applied to a subject with closed eyes at rest, such that the subject is unable to tell that they are rotating.

In some embodiments, a subject experiences an angular acceleration such that the subject is unable to tell that they are rotating until the subject reaches a predetermined angular velocity, at which time the rotation comes to rest in a time period of 1 second or less. In some embodiments, the predetermined angular velocity is determined by Equation 1:

$$\text{Angular Velocity}(^\circ/\text{second}) = (x+120)(1-y^8) \quad \text{(Equation 1)}$$

where x is the age of the subject, and y is the ratio between the slow phase velocity on the subject's right side to the slow phase velocity of nystagmus on the subject's left side. The angular velocity experienced by a subject before coming to rest may range between 50°/second and 250°/second. The above equation is provided as an example of applying rotary stimulation to a subject in order to treat a mood disorder in the subject, and should not be considered limiting. Any sequence in which accelerating rotary stimulation is applied to a subject followed by the subject coming to rest may be used.

In some embodiments, therapeutic vestibular stimulation comprises caloric stimulation. In such embodiments, therapeutic vestibular stimulation may comprise caloric stimulation via, for example, the application of hot air to the subject's right and/or left ear. The air may be at a temperature greater than the subject's body temperature, with a preferred temperature of approximately 49° Celsius. The caloric stimulation may be applied to a subject for any length of time, for example for approximately one minute.

In some embodiments, therapeutic vestibular stimulation comprises optokinetic stimulation. In such embodiments, optokinetic stimulation may comprise angular acceleration to the subject' left and/or right side, for example at a rate of 0.1-2°/second$^2$. Angular acceleration may also be provided such that a subject begins at rest, has an increasing velocity for a period of time (via a positive angular acceleration) and then has a decreasing velocity for a period of time (via a negative angular acceleration), then coming to rest.

Treatment may be performed on a subject of any age, but preferably on a subject with an age between about 16 and 90 years. In some embodiments, treatment comprises one or more sessions. For example, treatment may comprise three sessions, or may comprise any number of sessions until a subject no longer experiences symptoms associated with a mood disorder. In some embodiments, treatment sessions are one week apart, although any suitable length of time between treatment sessions may be used. An example of a treatment session is described below in relation to FIG. 8.

EXEMPLARY EMBODIMENTS

Figure 6:
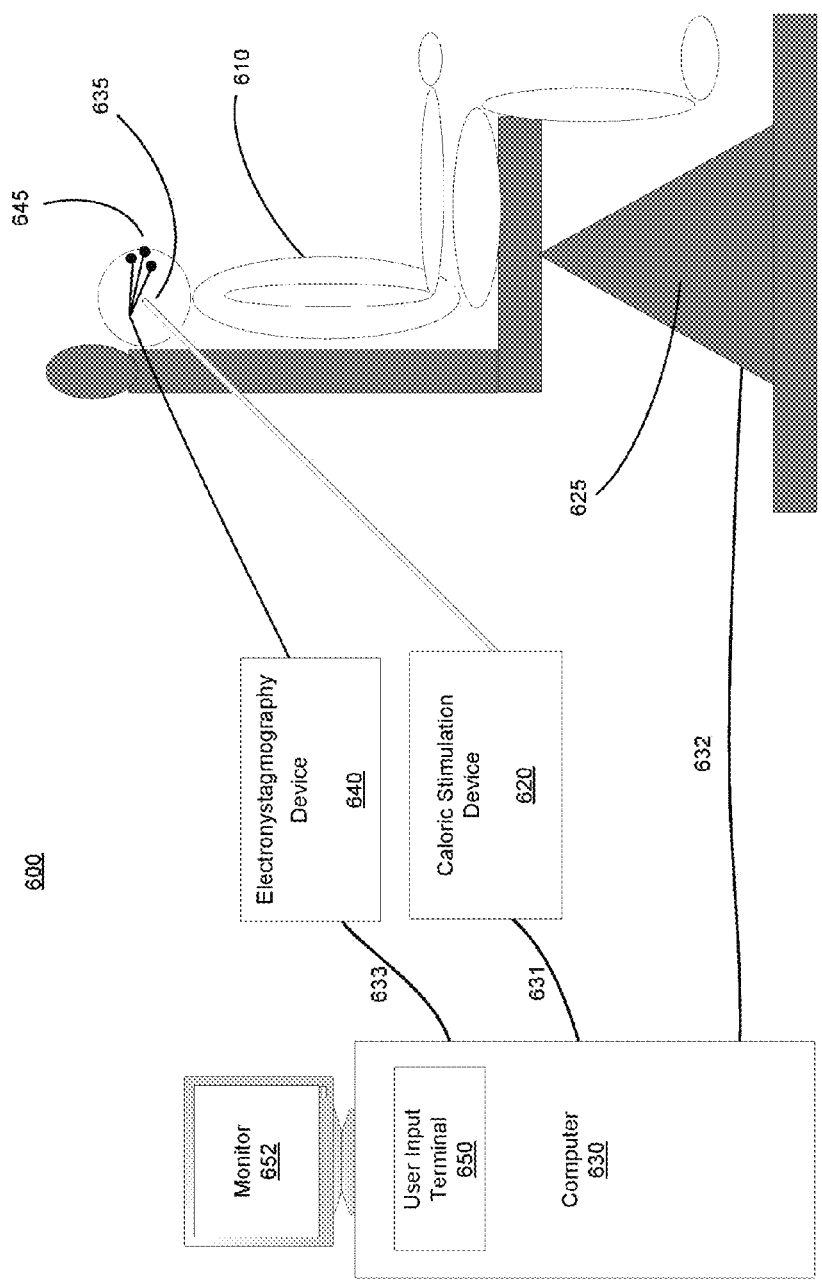
FIG. 6 is a schematic depicting an exemplary system for practicing some embodiments of the disclosure.

FIG. 6 depicts an exemplary embodiment of the disclosure, which may be used to diagnose depression in a subject and/or treat a mood disorder in a subject. In the example of FIG. 6, system 600 provides for diagnosis and/or treatment of a mood disorder for subject 610. Subject 610 may have previously been diagnosed with a mood disorder and system 600 is to be used to treat the mood disorder in the subject. Alternatively, subject 610 may be an individual to be evaluated by system 600 in order to diagnose the subject with a mood disorder, and may additionally be treated by system 600 for a mood disorder.

In some embodiments, one or more apparatuses for stimulating the vestibular system of subject 610, such as caloric stimulation device 620 and rotary chair 625, are provided. However, these apparatuses are shown in FIG. 6 as examples only, and any suitable device for stimulating the vestibular system of subject 610 may be utilized, including those described above.

Caloric stimulation device 620 delivers water or air to subject 610's ear canal 635 in order to stimulate the subject's vestibular system on one side. Caloric stimulation device 620 may be controlled by computer 630 via interface 631, and rotary chair 625 may be controlled by computer 630 via interface 632. Computer 630 may, via interfaces 631 and 632, allow an operator of system 600 to automatically operate one or more devices for stimulating the vestibular system of subject 610, such as caloric stimulation device 620 and rotary chair 625.

In some embodiments, computer 630 is operated to register subject 610's response to vestibular stimulation, such as that provided by caloric stimulation device 620 or rotary chair 625. This may be performed by electronystagmography system 640 coupled to electrodes 645 that monitor nystagmus of subject 610, and coupled to computer 630 to which data is provided from electrodes 645 via interface 633. Other suitable devices to register a subject's response to vestibular stimulation may also be used.

In some embodiments, computer 630 is to be configured and/or operated by an operator (not shown in FIG. 6) via user input terminal 650 and monitor 652. Alternatively, computer 630 may be configured to automatically perform diagnosis and/or treatment of subject 610. It will be appreciated by those of skill in the art that a computer providing varying levels of automated and operator-performed actions may be utilized in system 600, and that any number or type of input and output devices, such as a user input terminal or monitor, may be used.

In some embodiments, diagnosis of a mood disorder is performed by registering subject 610's response to vestibular stimulation. Such vestibular stimulation may be provided, for example, by caloric stimulation device 620 or rotary chair 625, though may also be provided via any suitable means of vestibular stimulation. In some embodiments, diagnosis of a mood disorder is performed using measurements of nystagmus or via analysis performed on measurements of nystagmus. For example, the ratio between the slow phase velocity of nystagmus on the subject's right side to the slow phase velocity of nystagmus on the subject's left side may be used to diagnose a mood disorder in the subject.

In some embodiments, therapeutic vestibular stimulation may be applied to subject 610 via system 600 in order to treat a mood disorder in the subject. Such stimulation may be based on subject 610's response to vestibular stimulation provided via caloric stimulation device 620 and/or rotary chair 625. Any suitable method of providing therapeutic vestibular stimulation based on the subject's response to vestibular stimulation may be used. For example, therapeutic vestibular stimulation performed in order to treat a mood disorder in the subject may be based on measurements of nystagmus or analysis performed on measurements of nystagmus. Attributes associated with subject 610, such as the subject's age, weight or height, may also be used.

In some embodiments, electronystagmography system 640 measures nystagmus of subject 610 during caloric stimulation of the subject's left ear and during caloric stimulation of the subject's right ear via caloric stimulation device 620, and provides the measurements to computer 630. Electronystagmography system 640 may also be used to measure nystagmus of subject 610 during rotary stimulation of the subject via rotary chair 625.

In some embodiments, computer 630 automatically determines therapeutic vestibular stimulation to be applied to subject 610 in order to treat a mood disorder in the subject, and may also automatically apply said determined vestibular stimulation to the subject. For example, computer 630 may use nystagmus measurements to determine the slow phase velocity of nystagmus during rotary stimulation of the subject's right side, and to determine the slow phase velocity of nystagmus during rotary stimulation of the subject's left side. In such an example, computer 630 may determine the ratio between the slow phase velocity of nystagmus on the subject's right side to the slow phase velocity of nystagmus on the subject's left side, and may apply therapeutic vestibular stimulation to subject 610 based on the determined ratio.

In some embodiments, therapeutic vestibular stimulation applied to treat a mood disorder in subject 610 comprises rotary stimulation, wherein the subject is rotating at an increasing speed, for example in rotary chair 625. System 600 may be used in any suitable way to treat a mood disorder in subject 610, such as those described above, and those described below in relation to FIG. 8. In some embodiments, computer 630 automatically operates vestibular stimulation devices such as rotary chair 625 in order to apply therapeutic vestibular stimulation.

Figure 7:
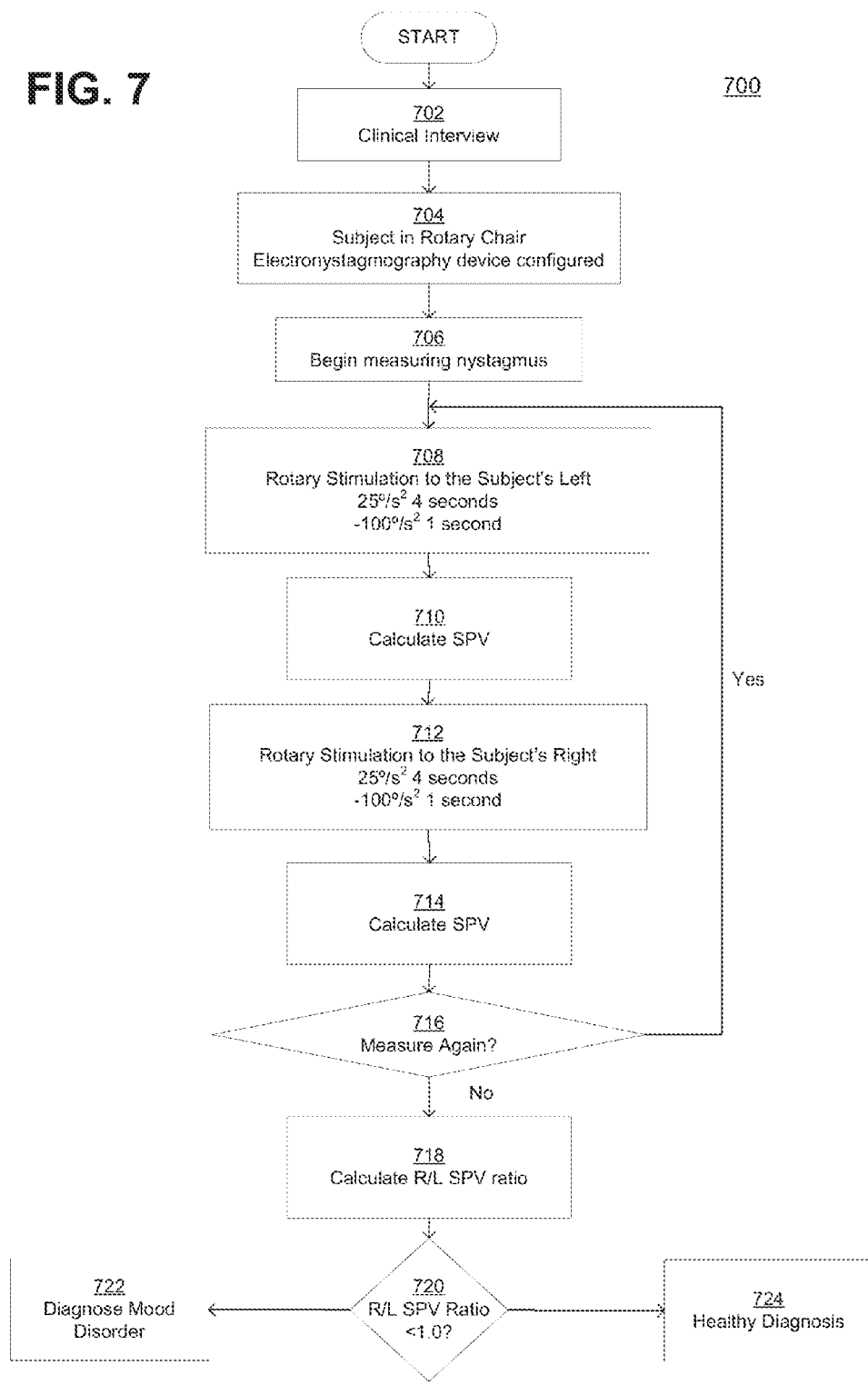
FIG. 7 is a flow chart showing how diagnosis of a mood disorder may be performed, according to some embodiments.

FIG. 7 is a flow chart illustrating steps that may be followed, for some embodiments of the disclosure, to diagnose a subject with a mood disorder. Process 700 starts with step 702, in which a subject receives a clinical interview. A clinical interview may comprise any psychological assessment of a subject, for example the Hamilton Depression Scale Rating (HAM-D), or the Beck Depression Inventory (BDI). Biographical or historical information, such as a subject's age, weight, profession, mental health history, etc. may also be obtained during a clinical interview.

The clinical interview in step 702 may be performed by a doctor, nurse, or other health professional asking questions of a subject, but may also comprise an automated computing device operated to obtain information from a subject relating to their mental health. The clinical interview may also be conducted at a different time to the steps which follow.

In step 704 the subject is seated in a rotary chair and an electronystagmography device is attached the subject. The rotary chair and nystagmography device may be of the type and configuration such as those described above. In particular, the rotary chair may be capable of being operated automatically by a suitably programmed computing device. In the example of FIG. 7, an electronystagmography device is used, although any suitable device capable of measuring nystagmus of the subject may be used.

In step 706, the electronystagmography device is configured to begin registering the subject's eyes. In step 708, the rotary chair is operated to move to the subject's left comprising an acceleration of approximately $25°/\text{second}^2$ for a period of 4 seconds, followed by a deceleration such that the subject returns to rest over 1 second. The subject's nystagmus may be measured during the acceleration and/or deceleration phases.

In step 710, the slow phase velocity of the subject's right side is measured, based on the measured nystagmus of the subject during step 708. The slow phase velocity may be calculated via any suitable method, including by a computing device configured to calculate the slow phase velocity of nystagmus from electronystagmography data.

In step 712, the rotary chair is operated to move to the subject's right comprising an acceleration of approximately $25°/\text{second}^2$ for a period of 4 seconds, followed by a deceleration such that the subject returns to rest over 1 second. The subject's nystagmus may be measured during the acceleration and/or deceleration phases.

In step 714, the slow phase velocity of the subject's left side is measured based on the measured nystagmus of the subject during step 712.

In step 716, a determination is made whether to perform further diagnostic measurements of the subject. Such a determination may be made for any reason, including to obtain multiple measurements of nystagmus on each side of the subject, and to improve the accuracy of the slow phase velocity measurements. Repeated measurements may be performed on the left and/or right side (i.e., steps 708 and 710, or steps 712 and 714, may be optionally skipped after step 716).

In step 718, a ratio is determined between the slow phase velocity of nystagmus on the subject's right side determined in step 710, and the slow phase velocity of nystagmus on the subject's left side determined in step 714.

In step 720, the ratio determined in step 718 is compared with a value of 1.0, representing a slow phase velocity of nystagmus on the subject's right side that is equal to the slow phase velocity of nystagmus on the subject's left side. If the ratio determined in step 718 is less than 1.0, in step 722 a diagnosis of a mood disorder is identified. Such a determination corresponds to a slow phase velocity of nystagmus on the subject's right side that is less than the slow phase velocity of nystagmus on the subject's left side, which may imply that the subject's right vestibular system has diminished functioning. If the ratio determined in step 718 is equal to or greater than 1.0, a healthy diagnosis is identified in step 724.

Any suitable mathematical combination of the slow phase velocity of nystagmus on the subject's right side and the slow phase velocity of nystagmus on the subject's left side may be used in steps 718 and 720.

Process 700 may be conducted by one or more individuals, such as health professionals, and may be performed in a partial or completely automated fashion. For example, a technician may perform process 700 wherein the movement of the rotary chair is performed automatically by a suitable computing device. Alternatively, process 700 may be performed in a completely automated fashion by, for example, via a booth containing a rotary chair which measures the slow phase velocity of nystagmus of a subject on the right and left sides, and identifies a diagnosis of a mood disorder based on the measurements.

Figure 8:
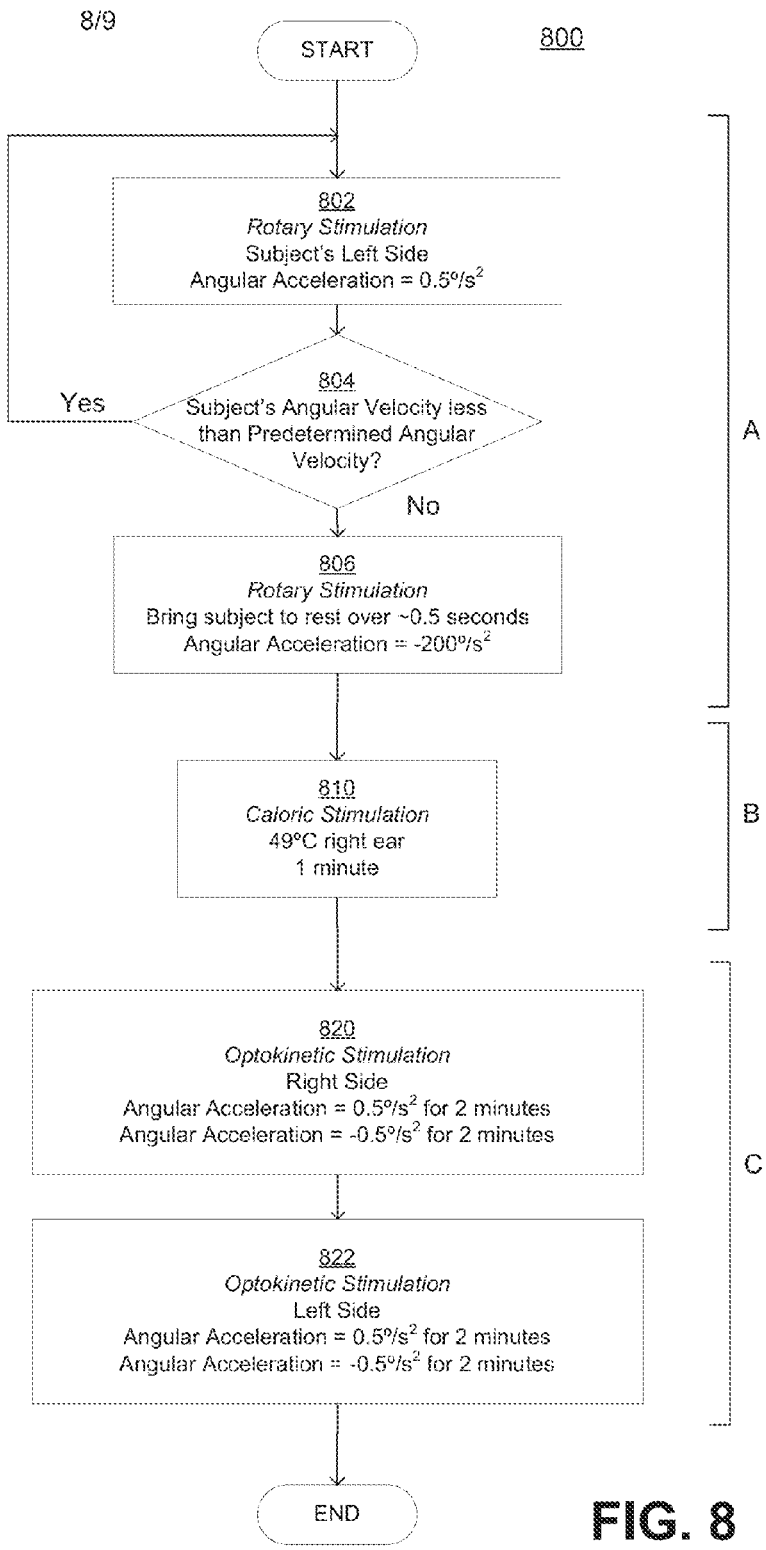
FIG. 8 is a flow chart showing how treatment of a mood disorder may be performed, according to some embodiments.

FIG. 8 is a flow chart illustrating steps that may be followed, for some embodiments of the disclosure, to treating a mood disorder in a subject.

Process 800, shown in FIG. 8, may be performed to treat a mood disorder in a subject. The subject of process 800 may have been previously diagnosed with a mood disorder, for example via process 700 of FIG. 7, or via any suitable method. Data for performing therapeutic vestibular stimulation of the subject in order to treat a mood disorder in the subject may be obtained via any suitable means, including by performing process 700 of FIG. 7. However, there is no requirement that process 700 is performed prior to process 800, and data for performing therapeutic vestibular stimulation of the subject may be provided by a third party not directly involved with the performing of process 800.

Regardless of the events preceding process 800, process 800 begins with rotary stimulation of the subject in steps 802, 804 and 806, labeled as group A in FIG. 8.

In step 802, rotary stimulation is applied to a subject's left side. In the example of FIG. 8, the subject's eyes remain closed while an angular acceleration of approximately $0.5°/(second)^2$ is applied. However, any suitable angular acceleration may be used such that the subject is unable to tell that they are moving.

In step 804, the angular velocity of the subject is compared with a predetermined angular velocity. The predetermined angular velocity may be determined in any suitable way, for example via Equation (1) above. The comparison of angular velocities may be performed in any suitable way, including by a computing device connected to a rotary chair. The comparison in step 804 may also be performed at any suitable time interval after step 802 begins, for example 1 millisecond or 1 second after step 802 begins. In some embodiments, the duration of step 802 depends on the predetermined angular velocity.

If, in step 804, it is determined that the angular velocity of the subject is less than the predetermined angular velocity, flow returns to step 802 to continue application of the angular acceleration to the subject. If, in step 804, it is determined that the angular velocity of the subject is equal or greater than the predetermined angular velocity, flow continues to step 806. It will be appreciated by those of skill in the art that the comparison of step 804 may be performed in parallel to the application of rotary stimulation to the subject, and that the comparison of step 804 may be performed without interruption of the application of said rotary stimulation.

In step 806, an angular acceleration of approximately $-200°/(second)^2$ is applied in order to bring the subject quickly to rest and thereby to stimulate the right side of the subject's vestibular system.

In step 810 and group B, caloric stimulation to the subject's right ear is applied via the application of air at 49° Celsius to the subject's ear canal. In the example of FIG. 8, the caloric stimulation of the subject's right ear is applied for 1 minute.

Steps 820 and 822 comprise group C wherein optokinetic stimulation is applied to the subject. In step 820, optokinetic stimulation is applied to the subject's right side. An angular acceleration of $0.5°/second^2$ is applied to the subject at rest for a period of 2 minutes, after which the subject experiences an angular velocity of 100°/second. This is followed by an angular acceleration of $-0.5°/second^2$ applied to the subject for a period of 2 minutes, after which the subject has returned to rest.

In step 822, optokinetic stimulation is applied to the subject's left side. Step 822 may be the same as step 820 but performed on the opposite side of the subject.

The therapeutic vestibular performed in groups A, B and C of FIG. 8 may be performed any number of times, in any combination, and in any order to treat a mood disorder in a subject. For example, group B alone may be performed, or group C then group A may be performed.

It will further be appreciated that process 800 is provided as an exemplary embodiment for treating a mood disorder and that treating a mood disorder need not be limited to the particular details of process 800. The particular timing, angular velocities, angular accelerations and temperatures provided in FIG. 8, are provided as exemplary embodiments and the invention of the present disclosure is not limited to these particular applications of the concepts described herein. For example, the angular velocities and angular accelerations applied to a subject in process 800 are provided as exemplary embodiments, as other angular velocities and angular acceleration values could also be used. Additionally, steps of process 800 where only one side of the subject's vestibular system is stimulated are also provided as exemplary embodiments, as either side of the subject's vestibular system may, in general, be stimulated at any step while treating a mood disorder in the subject.

Tables 1, 2 and 3 present clinical data regarding subjects that have been diagnosed and treated for a mood disorder.

Tables 1 and 2 depict experimental data for 45 subjects in a clinical trial to determine the effectiveness of treating depression via therapeutic vestibular stimulation. 15 subjects were assigned to a placebo control group, and are shown in Table 1. The remaining 30 subjects were assigned to an experimental group and are shown in Table 2.

TABLE 1

PLACEBO-CONTROL GROUP

| Patient ID | Sex | Before Placebo Hamilton Depression Scale Rating | After Placebo Hamilton Depression Scale Rating | Before Placebo R/L SPV Ratio | After Placebo R/L SPV Ratio |
|---|---|---|---|---|---|
| 1 | F | 23 | 10 | 0.68 | 0.61 |
| 2 | F | 16 | 18 | 1.10 | 0.93 |
| 3 | F | 24 | 35 | 1.25 | 1.15 |
| 4 | F | 15 | 20 | 0.65 | 1.63 |
| 5 | F | 16 | 23 | 0.68 | 0.57 |
| 6 | F | 20 | 33 | 0.95 | 0.89 |
| 7 | F | 21 | 21 | 0.97 | 0.52 |
| 8 | F | 16 | 10 | 0.80 | 1.52 |
| 9 | F | 23 | 16 | 0.40 | 0.21 |
| 10 | F | 16 | 15 | 0.59 | 0.58 |
| 11 | M | 16 | 19 | 0.63 | 0.56 |
| 12 | F | 32 |  | 0.70 | 0.47 |
| 13 | F | 32 | 10 | 0.98 | 1.53 |
| 14 | F | 37 | 35 | 0.86 | 0.70 |
| 15 | F | 23 | 36 | 0.45 | 1.00 |
| Mean Values |  | 22.00 | 21.50 | 0.78 | 0.86 |

TABLE 2

EXPERIMENTAL GROUP

| Patient ID | Sex | Before Treatment Hamilton Depression Scale Rating | After Treatment Hamilton Depression Scale Rating | Before Treatment R/L SPV Ratio | After Treatment R/L SPV Ratio |
|---|---|---|---|---|---|
| 21 | M | 16 | 13 | 0.63 | 1.00 |
| 22 | F | 14 | 6 | 0.27 | 0.82 |

TABLE 2-continued

EXPERIMENTAL GROUP

| Patient ID | Sex | Before Treatment Hamilton Depression Scale Rating | After Treatment Hamilton Depression Scale Rating | Before Treatment R/L SPV Ratio | After Treatment R/L SPV Ratio |
|---|---|---|---|---|---|
| 23 | F | 40 | 6 | 1.25 | 0.72 |
| 24 | F | 23 | 18 | 0.38 | 0.41 |
| 25 | M | 16 | 4 | 0.63 | 1.15 |
| 26 | F | 26 | 24 | 1.48 | 1.20 |
| 27 | F | 19 | 3 | 0.84 | 0.52 |
| 28 | F | 39 | 8 | 0.63 | 0.90 |
| 29 | F | 39 | 2 | 0.75 | 0.95 |
| 30 | F | 22 | 6 | 0.54 | 1.29 |
| 31 | F | 18 | 0 | 0.63 | 2.35 |
| 32 | F | 13 | 1 | 0.57 | 0.64 |
| 33 | F | 36 |  | 0.82 | 0.46 |
| 34 | F | 37 | 8 | 0.77 | 0.82 |
| 35 | F | 23 | 18 | 0.57 | 0.56 |
| 36 | F | 32 | 5 | 1.00 | 0.76 |
| 37 | F | 15 | 5 | 0.57 | 1.21 |
| 38 | F | 16 | 10 | 0.25 | 0.52 |
| 39 | F | 20 | 18 | 0.52 | 0.51 |
| 40 | F | 31 | 5 | 0.50 | 0.90 |
| 41 | M | 25 | 12 | 0.75 | 0.96 |
| 42 | F | 18 | 21 | 0.79 | 0.96 |
| 43 | F | 13 | 9 | 1.32 | 1.21 |
| 44 | F | 26 | 6 | 0.59 | 0.88 |
| 45 | F | 34 | 2 | 0.74 | 0.91 |
| 46 | M | 35 | 14 | 0.73 | 1.13 |
| 47 | M | 24 | 0 | 0.75 | 1.25 |
| 48 | F | 27 | 2 | 0.30 | 0.89 |
| 49 | M | 34 | 9 | 0.73 | 1.10 |
| 50 | M | 30 | 8 | 0.78 | 1.50 |
| Mean Values |  | 25.37 | 8.38 | 0.70 | 0.95 |

Table 3 is a summary of the experimental data shown in Tables 1 and 2, showing a decrease in the Hamilton Depression Scale Rating of the experimental group over the placebo group, and an increase in the measured ratio of slow phase velocity of nystagmus on the subject's right side to the slow phase velocity of nystagmus on the subject's left side for the experimental group over the placebo group.

TABLE 3

|  | Hamilton Depression Scale Rating BEFORE Treatment Or Placebo | Hamilton Depression Scale Rating POST Treatment or Placebo | R/L SPV Ratio BEFORE Treatment or Placebo | R/L SPV Ratio POST Treatment or Placebo |
|---|---|---|---|---|
| Control (Placebo) Group | 22 | 21.5 | 0.78 | 0.86 |
| Experimental Group (Vestibular Stimulation) | 25.37 | 8.38 | 0.70 | 0.95 |

Figure 9:
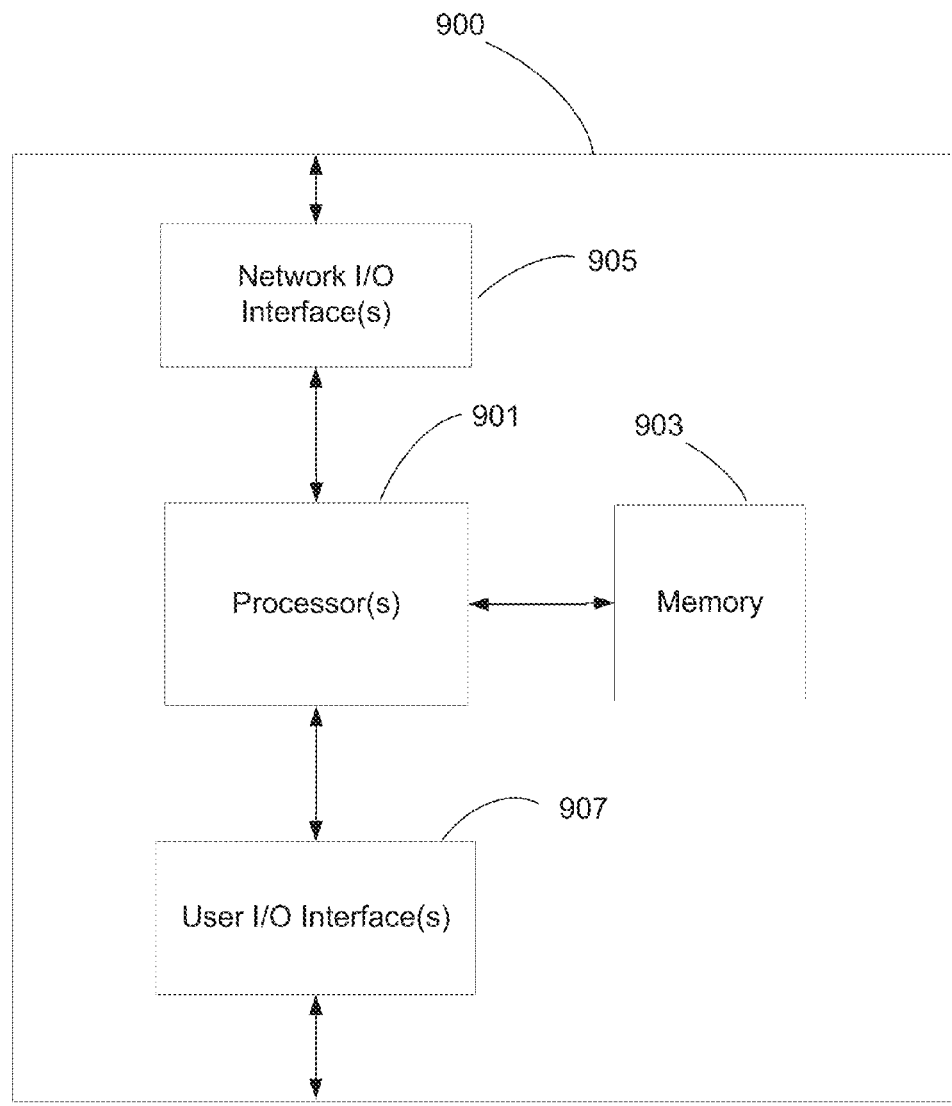
FIG. 9 is a schematic of a computing device suitable for practicing some embodiments of the disclosure.

FIG. 9 is a block diagram of an illustrative computing device 900 that may be used to implement any aspect of the disclosure.

Computing device 900 may include one or more processors 901 and one or more tangible, non-transitory computer-readable storage media (e.g., memory 903). Memory 903 may store, in tangible non-transitory computer-readable storage media computer program instructions that implement any of the above-described functionality. Processor(s) 901 may be coupled to memory 903 and may execute such computer program instructions to cause the functionality to be realized and performed.

Computing device 900 may also include a network input/output (I/O) interface 905 via which the computing device may communicate with other computers (e.g., over a network), and may also include one or more user I/O interfaces, via which the computer may provide output to and receive input from a user. The user I/O interfaces may include devices such as a keyboard, a mouse, a microphone, a display device (e.g., a monitor or touch screen), speakers, a camera, and/or various other types of I/O devices.

Having thus described several aspects of at least one embodiment of this disclosure, it is to be appreciated that various alterations, modifications, and improvements will readily occur to those skilled in the art.

Such alterations, modifications, and improvements are intended to be part of this disclosure, and are intended to be within the spirit and scope of the disclosure. Further, though advantages of the present disclosure are indicated, it should be appreciated that not every embodiment of the disclosure will include every described advantage. Some embodiments may not implement any features described as advantageous herein and in some instances. Accordingly, the foregoing description and drawings are by way of example only.

The above-described embodiments of the present disclosure can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be implemented via software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, an aspect of the disclosure is that such methods may be implemented via a tangible, non-transitory computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform those methods and implement the various embodiments of the disclosure discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present disclosure as discussed above. As used herein, the term "computer-readable storage medium" encompasses only a computer-readable medium that can be considered to be a manufacture (i.e., article of manufacture) or a machine. Alternatively or additionally, the disclosure may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the disclosure may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of treating depression in a subject, the method comprising:
   (a) applying diagnostic vestibular stimulation to a subject, the diagnostic vestibular stimulation comprising rotary, caloric and/or optokinetic stimulation;
   (b) registering the subject's response to the diagnostic vestibular stimulation, said registering comprising measuring an asymmetry between a right side of the subject's vestibular system and a left side of the subject's vestibular system; and
   (c) treating depression in the subject by applying therapeutic vestibular stimulation to the subject using at least one apparatus, the therapeutic vestibular stimulation determined using at least one processor based on the asymmetry measured in response to the diagnostic vestibular stimulation, the therapeutic vestibular stimulation comprising rotary, caloric and/or optokinetic stimulation,
   wherein the therapeutic vestibular stimulation is configured to stimulate the left side of the subject's vestibular system and the right side of the subject's vestibular system in a different manner, and
   wherein the different manner between said stimulation of the left side of the subject's vestibular system and the right side of the subject's vestibular system is determined, by the at least one processor, based on the registered response to the diagnostic vestibular stimulation.

2. The method of claim 1, wherein registering the subject's response to the diagnostic vestibular stimulation comprises using at least one device to register nystagmus in the subject.

3. The method of claim 1, wherein the therapeutic vestibular stimulation comprises applying rotary stimulation to the subject, and wherein the rotary stimulation comprises at least one of:
   (1) angular acceleration in the range $0.1°/(second)^2$ to $2°/(second)^2$; or
   (2) angular acceleration in the range $50°/(second)^2$ to $500°/(second)^2$ to bring the subject to rest.

4. The method of claim 1, wherein the therapeutic vestibular stimulation comprises optokinetic stimulation, wherein the subject is at rest during optokinetic stimulation and wherein the optokinetic stimulation comprises moving visual stimuli.

5. The method of claim 1, wherein the therapeutic vestibular stimulation comprises inducing nystagmus in the subject.

6. The method of claim 1, wherein:
   registering the subject's response to the diagnostic vestibular stimulation comprises determining a ratio of the slow phase velocity of nystagmus during diagnostic vestibular stimulation to the subject's right side to the slow phase velocity of nystagmus during diagnostic vestibular stimulation to the subject's left side; and
   applying the therapeutic vestibular stimulation to the subject is based at least partly on said ratio.

7. The method of claim 1, wherein the therapeutic vestibular stimulation is based on the age of the subject.

8. The method of claim 1, wherein the different manner between said stimulation of the left side of the subject's vestibular system and the right side of the subject's vestibular system includes rotary stimulation that simulates the left side of the subject's vestibular system a greater amount than the rotary stimulation stimulates the right side of the subject's vestibular system.

9. The method of claim 1, wherein the different manner between said stimulation of the left side of the subject's vestibular system and the right side of the subject's vestibular system includes applying greater caloric stimulation to the subject's right ear compared with any concurrent application of caloric stimulation to the subject's left ear.

10. A system for use in treating depression in a subject, the system comprising:
    at least one processor; and
    a tangible, non-transitory computer recordable and readable medium operatively coupled to the at least one processor, the medium storing computer program instructions that, when executed by the at least one processor, cause the at least one processor to perform a method comprising:
    generating, based on an asymmetry between a right side of the subject's vestibular system and a left side of the subject's vestibular system measured by registering the subject's response to diagnostic vestibular stimulation, information to control at least one apparatus configured to treat depression by applying therapeutic vestibular stimulation to the subject,
    wherein the diagnostic vestibular stimulation comprises rotary, caloric and/or optokinetic stimulation,
    wherein the therapeutic vestibular stimulation comprises rotary, caloric and/or optokinetic stimulation and is configured to stimulate the left side of the subject's vestibular system and the right side of the subject's vestibular system in a different manner, and
    wherein the different manner between said stimulation of the left side of the subject's vestibular system and the right side of the subject's vestibular system is determined, by the at least one processor, based on the registered response to the diagnostic vestibular stimulation.

11. The system of claim 10, wherein the diagnostic vestibular stimulation comprises inducing nystagmus in the subject.

12. The system of claim 10, wherein the therapeutic vestibular stimulation comprises rotary stimulation, and wherein the rotary stimulation comprises at least one of:
    (1) angular acceleration in the range $0.1°/(second)^2$ to $2°/(second)^2$; and (2) angular acceleration in the range 50°/(second)² to 500°/(second)² to bring the subject to rest.

13. The system of claim 10, wherein the therapeutic vestibular stimulation comprises optokinetic stimulation, wherein the subject is at rest during optokinetic stimulation and wherein the optokinetic stimulation comprises moving visual stimuli.

14. The system of claim 10, wherein the therapeutic vestibular stimulation comprises inducing nystagmus in the subject.

15. The system of claim 10, wherein the asymmetry between the right side of the subject's vestibular system and the left side of the subject's vestibular system measured by registering the subject's response to diagnostic vestibular stimulation comprises a ratio of the slow phase velocity of nystagmus during diagnostic vestibular stimulation to the subject's right side to the slow phase velocity of nystagmus during diagnostic vestibular stimulation to the subject's left side.

16. The system of claim 10, wherein the therapeutic vestibular stimulation is based on the age of the subject.

17. The system of claim 10, wherein the different manner between said stimulation of the left side of the subject's vestibular system and the right side of the subject's vestibular system includes rotary stimulation that simulates the left side of the subject's vestibular system a greater amount than the rotary stimulation stimulates the right side of the subject's vestibular system.

18. The system of claim 10, wherein the different manner between said stimulation of the left side of the subject's vestibular system and the right side of the subject's vestibular system includes applying greater caloric stimulation to the subject's right ear compared with any concurrent application of caloric stimulation to the subject's left ear.

19. An apparatus for treating depression in a subject, the apparatus comprising:
(a) one or more devices for applying therapeutic vestibular stimulation comprising rotary, caloric and/or optokinetic stimulation to the subject;
(b) an interface for automatically operating said one or more devices;
(c) at least one processor; and
(d) at least one computer readable medium encoded with a program that, when executed by the at least one processor, performs a therapeutic method, the method comprising:
obtaining data to control the one or more devices to treat depression in the subject by applying therapeutic vestibular stimulation to the subject, the data indicating a measured asymmetry between a right side of the subject's vestibular system and a left side of the subject's vestibular system; and
via the interface, operating the one or more devices to treat the depression in the subject by applying therapeutic vestibular stimulation to the subject based on the data,
wherein the therapeutic vestibular stimulation is configured to stimulate a left side of the subject's vestibular system and a right side of the subject's vestibular system in a different manner, and
wherein the different manner between said stimulation of the left side of the subject's vestibular system and the right side of the subject's vestibular system is determined, by the at least one processor, based on the data indicating the measured asymmetry.

20. The apparatus of claim 19, wherein the therapeutic vestibular stimulation applied to the subject comprises rotary stimulation, and wherein the rotary stimulation comprises at least one of:
(1) angular acceleration in the range 0.1°/(second)² to 2°/(second)²; and
(2) angular acceleration in the range 50°/(second)² to 500°/(second)² to bring the subject to rest.

21. The apparatus of claim 19, wherein the therapeutic vestibular stimulation comprises optokinetic stimulation, wherein the subject is at rest during optokinetic stimulation and wherein the optokinetic stimulation comprises moving visual stimuli.

22. The apparatus of claim 19, wherein the therapeutic vestibular stimulation comprises inducing nystagmus in the subject.

23. The apparatus of claim 19, wherein the data indicating a measured asymmetry between the right side of the subject's vestibular system and the left side of the subject's vestibular system comprises indicates a ratio of slow phase velocity of nystagmus during diagnostic vestibular stimulation to the subject's right side to slow phase velocity of nystagmus during diagnostic vestibular stimulation to the subject's left side.

24. The apparatus of claim 19, wherein the data indicates an age of the subject and wherein the therapeutic vestibular stimulation is based on the age of the subject.

25. The apparatus of claim 19, wherein the different manner between said stimulation of the left side of the subject's vestibular system and the right side of the subject's vestibular system includes rotary stimulation that simulates the left side of the subject's vestibular system a greater amount than the rotary stimulation stimulates the right side of the subject's vestibular system.

26. The apparatus of claim 19, wherein the different manner between said stimulation of the left side of the subject's vestibular system and the right side of the subject's vestibular system includes applying greater caloric stimulation to the subject's right ear compared with any concurrent application of caloric stimulation to the subject's left ear.

27. A tangible, non-transitory computer readable medium encoded with a program that, when executed by at least one processor, causes a suitable apparatus to perform a therapeutic method comprising:
treating depression in a subject by applying therapeutic vestibular stimulation to the subject using at least one apparatus, the therapeutic vestibular stimulation comprising rotary, caloric and/or optokinetic stimulation,
wherein the therapeutic vestibular stimulation is based on an asymmetry between a right side of the subject's vestibular system and a left side of the subject's vestibular system measured by registering the subject's response to diagnostic vestibular stimulation,
wherein the therapeutic vestibular stimulation is configured to stimulate a left side of the subject's vestibular system and a right side of the subject's vestibular system in a different manner, and
wherein the different manner between said stimulation of the left side of the subject's vestibular system and the right side of the subject's vestibular system is determined based on the registered response of the subject to the diagnostic vestibular stimulation.

28. The computer readable medium of claim 27, wherein the therapeutic vestibular stimulation comprises applying rotary stimulation, and wherein the rotary stimulation comprises at least one of:

(1) angular acceleration in the range 0.1°/(second)² to 2°/(second)²; or
(2) angular acceleration in the range 50°/(second)² to 500°/(second)² to bring the subject to rest.

29. The tangible, non-transitory computer readable medium of claim 27, wherein the therapeutic vestibular stimulation comprises optokinetic stimulation, wherein the subject is at rest during optokinetic stimulation and wherein the optokinetic stimulation comprises moving visual stimuli.

30. The tangible, non-transitory computer readable medium of claim 27, wherein the therapeutic vestibular stimulation comprises inducing nystagmus in the subject.

31. The tangible, non-transitory computer readable medium of claim 27, wherein the asymmetry between the right side of the subject's vestibular system and the left side of the subject's vestibular system measured by registering the subject's response to diagnostic vestibular stimulation comprises a ratio of the slow phase velocity of nystagmus during diagnostic vestibular stimulation to the subject's right side to the slow phase velocity of nystagmus during diagnostic vestibular stimulation to the subject's left side.

32. The tangible, non-transitory computer readable medium of claim 27, wherein the data indicates an age of the subject and wherein the therapeutic vestibular stimulation is based on the age of the subject.

33. The tangible, non-transitory computer readable medium of claim 27, wherein the different manner between said stimulation of the left side of the subject's vestibular system and the right side of the subject's vestibular system includes rotary stimulation that simulates the left side of the subject's vestibular system a greater amount than the rotary stimulation stimulates the right side of the subject's vestibular system.

34. The tangible, non-transitory computer readable medium of claim 27, wherein the different manner between said stimulation of the left side of the subject's vestibular system and the right side of the subject's vestibular system includes applying greater caloric stimulation to the subject's right ear compared with any concurrent application of caloric stimulation to the subject's left ear.

* * * * *